United States Patent
Biggerstaff et al.

(10) Patent No.: US 9,777,054 B2
(45) Date of Patent: Oct. 3, 2017

(54) SOLUBLE FIBRIN INHIBITORY PEPTIDES AND USES THEREOF

(75) Inventors: John Biggerstaff, Oak Ridge, TN (US); Brandy Weidow, Knoxville, TN (US)

(73) Assignee: ENSION INC., Pittsburgh, PA (US)

( * ) Notice: Subject to any disclaimer, the term of this patent is extended or adjusted under 35 U.S.C. 154(b) by 973 days.

(21) Appl. No.: 11/508,815

(22) Filed: Aug. 23, 2006

(65) Prior Publication Data

US 2007/0060522 A1    Mar. 15, 2007

Related U.S. Application Data

(60) Provisional application No. 60/710,684, filed on Aug. 23, 2006.

(51) Int. Cl.
| | |
|---|---|
| *C07K 14/75* | (2006.01) |
| *C07K 14/705* | (2006.01) |
| *G01N 33/50* | (2006.01) |
| *G01N 33/569* | (2006.01) |
| *A61K 38/00* | (2006.01) |

(52) U.S. Cl.
CPC ........ *C07K 14/75* (2013.01); *C07K 14/70525* (2013.01); *C07K 14/70553* (2013.01); *G01N 33/5044* (2013.01); *G01N 33/56972* (2013.01); *A61K 38/00* (2013.01)

(58) Field of Classification Search
None
See application file for complete search history.

(56) References Cited

U.S. PATENT DOCUMENTS

| | | | | |
|---|---|---|---|---|
| 5,919,754 A | * | 7/1999 | Altieri et al. ..................... | 514/2 |
| 6,083,902 A | | 7/2000 | Cederhom-Williams ........ | 514/2 |
| 2002/0064853 A1 | * | 5/2002 | Heinrikson et al. .......... | 435/200 |
| 2002/0168722 A1 | * | 11/2002 | Grieninger et al. ......... | 435/69.1 |
| 2004/0101511 A1 | * | 5/2004 | Young .......................... | 424/85.2 |

OTHER PUBLICATIONS

Simpson-Haidaris et al., Tumors and Fibrinogen, 2001, Annals New York Academy of Sciences, v936, pp. 406-425.*
Ugarova et al. JBC 1998 v273 pp. 22519-22527.*
Kinoshita et al (Chest v117 pp. 790-795).*
Align sequence tool (retrived from http://xylian.igh.cnrs.fr/bin/nph-align_query.pl on Mar. 31, 2009 1 page).*
Sawai et al ('Impact of single-residue mutations on the structure and function of ovisporin/novisporin antimicrobial peptides' Protein Engineering v15(3) 2002 pp. 225-232—printed as pp. 1-19).*
Takeda et al ('The effect of local immunotherapy for breast cancer using a mixture of OK-432 and fibrinogen supplemented with activated macrophages' Biotherapy v7 1994 pp. 47-54).*
Fibrinogen gamma sequence retrieved from http://www.ncbi.nlm.nih.gov/protein/223170?report=genbank&log$=prottop&blast_rank=18&RID=VBG4M6BF015 on Jun. 10, 2013, 1 page.*
Biggerstaff et al ('Soluble fibrin inhibits monocyte adherence and cytotoxicity against tumor cells:implications for cancer metastasis' Thrombosis Journal 2006 v4(12) 14 pages).*

* cited by examiner

*Primary Examiner* — Karlheinz R Skowronek
*Assistant Examiner* — Ronald Niebauer
(74) *Attorney, Agent, or Firm* — Blynn L. Shideler; Krisanne Shideler; BLK Law Group

(57) ABSTRACT

The present invention demonstrated that soluble fibrin binds to both Mac-1 and ICAM-1-expressing cells and inhibited adherence of these cells and immune cytotoxicity, thus inducing immune suppression in cancer. Additionally, the present invention also demonstrated that soluble fibrin enhanced metastasis in an in vivo model. Furthermore, the present invention demonstrated the utility of specific peptides that block binding of soluble fibrin to these cells as therapeutic agents in cancer progression and metastasis. It is further contemplated that these peptides can also be used to treat other diseases such as cardiovascular disease, arthritis and in many inflammatory responses where there is increased levels of soluble fibrin.

7 Claims, 8 Drawing Sheets

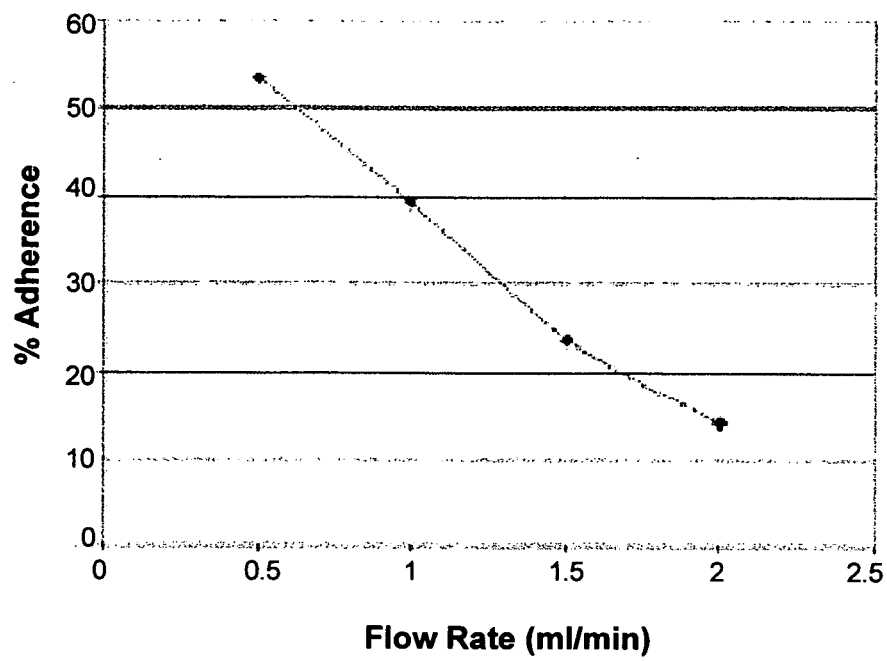
Fig. 10
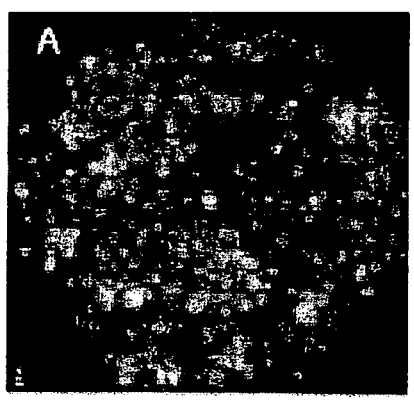 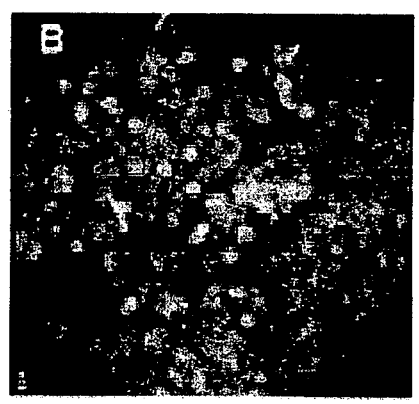
Fig. 11A        Fig. 11B

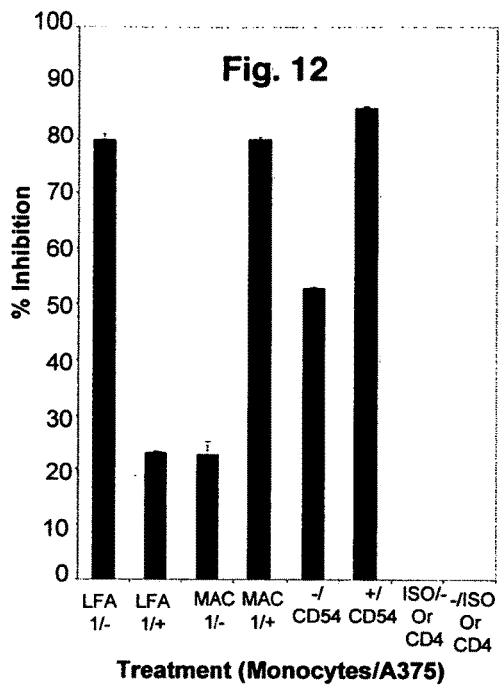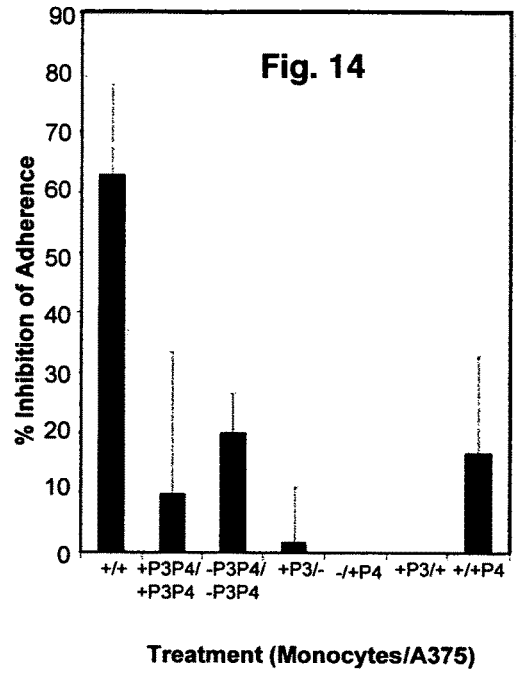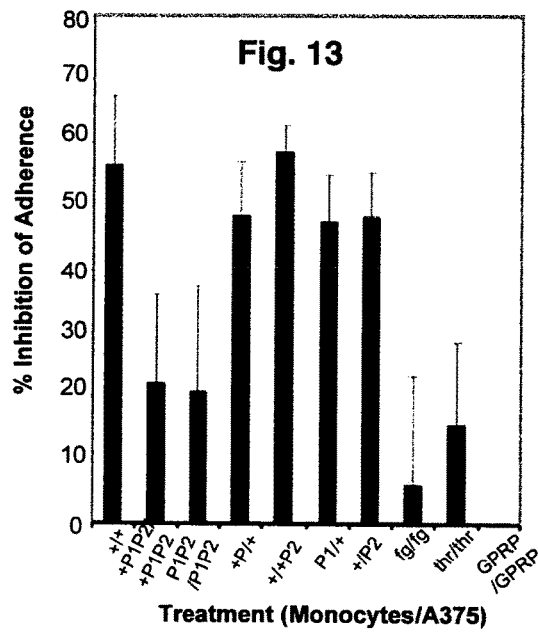

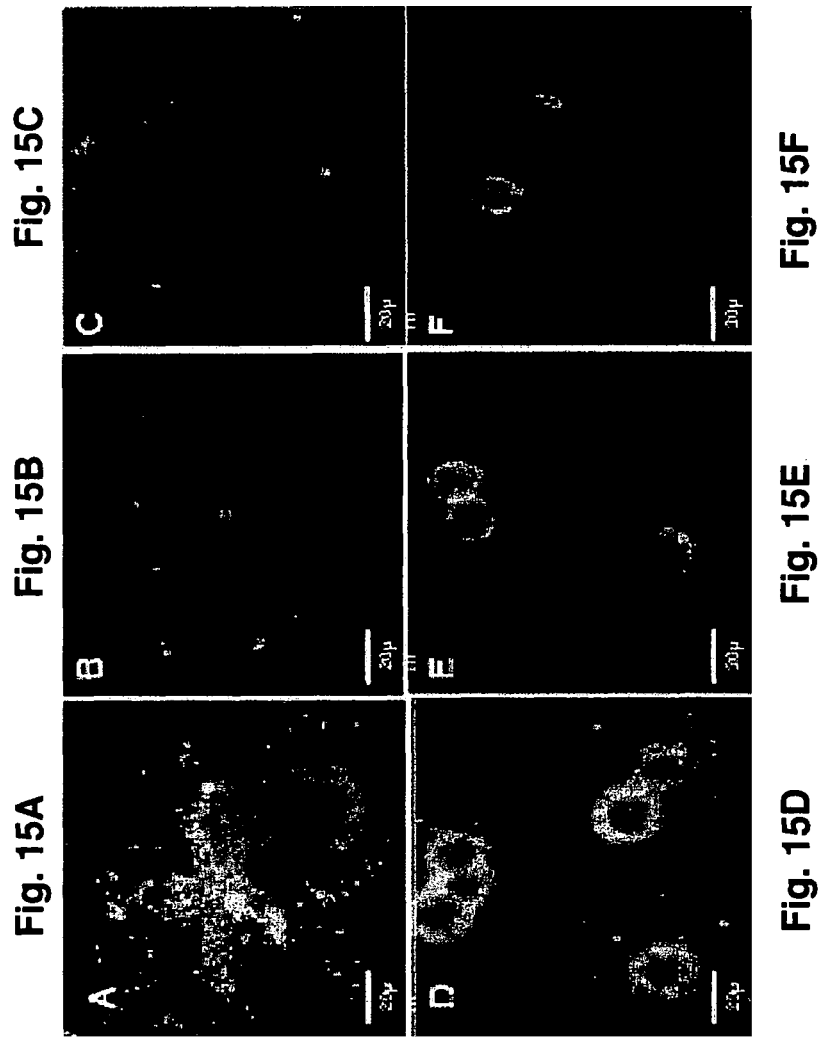

SEQUENCE LISTING

```
<160> NUMBER OF SEQ ID NOS: 7

<210> SEQ ID NO 1
<211> LENGTH: 17
<212> TYPE: PRT
<213> ORGANISM: Artificial
<220> FEATURE:
<221> NAME/KEY: CHAIN
<223> OTHER INFORMATION: a peptide comprising amino acids 245-261 of
      the alphaM I-domain on mac-1

<400> SEQUENCE: 1

Lys Phe Gly Asp Pro Leu Gly Tyr Glu Asp Val Ile Pro Glu Ala
                5                  10                  15

Asp Arg

<210> SEQ ID NO 2
<211> LENGTH: 19
<212> TYPE: PRT
<213> ORGANISM: Artificial
<220> FEATURE:
<221> NAME/KEY: CHAIN
<223> OTHER INFORMATION: peptide comprising amino acids 377-395
      on the fibrinogen gamma chain complementary
      to the alphaM I-domain sequence on mac1.

<400> SEQUENCE: 2

Tyr Lys Met Lys Lys Thr Thr Met Lys Ile Ile Pro Phe Asn Arg
                5                  10                  15
```

Leu Thr Ile Gly

<210> SEQ ID NO 3
<211> LENGTH: 14
<212> TYPE: PRT
<213> ORGANISM: Artificial
<220> FEATURE:
<221> NAME/KEY: CHAIN
<223> OTHER INFORMATION: peptide comprising amino acids 8-21 on the
      ICAM-1 first immunoglobulin domain

<400> SEQUENCE: 3

Lys Val Ile Leu Pro Arg Gly Gly Ser Val Leu Val Thr Cys
                 5                  10

<210> SEQ ID NO 4
<211> LENGTH: 16
<212> TYPE: PRT
<213> ORGANISM: Artificial
<220> FEATURE:
<221> NAME/KEY: CHAIN
<223> OTHER INFORMATION: peptide comprising amino acids 117-133
      of the fibrinogen gamma chain.

<400> SEQUENCE: 4

Asn Gln Lys Ile Val Asn Leu Lys Glu Lys Val Ala Gln Leu Glu
                 5                  10                  15

Ala

<210> SEQ ID NO 5
<211> LENGTH: 17
<212> TYPE: PRT
<213> ORGANISM: Artificial
<220> FEATURE:
<221> NAME/KEY: CHAIN
<223> OTHER INFORMATION: peptide comprising the cell-binding
      domain in soluble fibin.

<400> SEQUENCE: 5

Asn Asn Gln Lys Ile Val Asn Leu Lys Glu Lys Val Ala Gln Leu
                 5                  10                  15

Glu Ala

<210> SEQ ID NO 6
<211> LENGTH: 20
<212> TYPE: PRT
<213> ORGANISM: Artificial sequence
<220> FEATURE:
<221> NAME/KEY: CHAIN
<223> OTHER INFORMATION: peptide comprising the cell-binding
      domain in soluble fibin.

<400> SEQUENCE: 6

Tyr Lys Ser Met Lys Lys Thr Thr Met Lys Ile Ile Pro Phe Asn
                 5                  10                  15

Arg Leu Thr Ile Phe
                20

<210> SEQ ID NO 7
<211> LENGTH: 19
<212> TYPE: PRT
<213> ORGANISM: Artificial sequence
<220> FEATURE:
<221> NAME/KEY: CHAIN
<223> OTHER INFORMATION: peptide comprising the soluble fibrin
      protein-binding domain in soluble fibin -continued

```
<400> SEQUENCE: 7

Lys Phe Gly Asp Pro Leu Gly Tyr Glu Asp Val Ile Pro Glu Ala
                  5                  10                  15

Asp Arg Glu Gly
```

SOLUBLE FIBRIN INHIBITORY PEPTIDES AND USES THEREOF

CROSS REFERENCE TO RELATED APPLICATION

This non-provisional application claims benefit of provisional application U.S. Ser. No. 60/710,684 filed on Aug. 23, 2005.

BACKGROUND OF THE INVENTION

Field of the Invention

The present invention relates to the fields of blood coagulation and immunology. More specifically, the present invention discloses peptide sequences that inhibit soluble fibrin (sFn) binding to blood monocytes and melanoma cells and their use in a wide variety of diseases such as cancer, cardiovascular disease, arthritis and inflammation.

Description of the Related Art

A relationship between cancer and abnormalities of the coagulation system has been recognized for over 100 years. Thromboembolic disease (usually of unknown etiology), refractory to anticoagulant therapy, may be an early detectable sign of an underlying cancer, which could precede the onset of observable cancer by months or years. Although many cancer patients exhibit clinically significant hemostatic abnormalities, about 50% of all patients (>90% with metastasis) have abnormal laboratory coagulation parameters (Gouin-Thibault & Samama., 1999). The most commonly reported abnormalities are elevated fibrinogen, fibrinopeptide A (FPA), raised platelet count and prolonged prothrombin time. Several studies have also reported increased soluble fibrin monomer (Iversen et al., 1995; Nakagawa et al, 1994; Andrassy et al., 1980). Patients with disseminated intravascular coagulation (DIC) have increased levels of circulating soluble fibrin monomer (Rickles et al., 1992). Persistently elevated levels of prothrombin fragment 1.2, thrombin-anti-thrombin complexes and soluble fibrin monomer, far above those seen in most thrombophilias may suggest an undiagnosed malignancy (Duncan et al., 1997). The presence of soluble fibrin in blood has, until recently, been considered a benign marker of the presence of an ongoing coagulopathy.

Soluble Fibrin

Fibrinogen is a homo-dimer of three peptide chains, designated Aa, Bb, and g. The protease thrombin binds to the Bb chain and cleaves the A peptide, followed by the B peptide from fibrinogen, leaving a fibrin monomer subunit. At sufficient concentration (as in clot formation) fibrin monomers will spontaneously polymerize to form insoluble fibrin polymer (the clot). However, during the initial stages of disseminated intravascular coagulation (induced by cancer, inflammation, sepsis etc.), only small amounts of soluble fibrin monomer are produced, which are not proximal to others to cause polymerization. In this case some fibrin monomer binds to a molecule of fibrinogen forming a soluble fibrin/fibrinogen dimmer. As DIC worsens in disease, the likelihood fibrin monomers to contact other monomers increases. The monomers in contact with each other bind to form soluble fibrin oligomers, of increasing length as the concentration of monomers increases in worsening disease. Oligomers consisting of greater than about eight subunits become insoluble and thrombus formation proceeds. Thus, the term 'soluble fibrin' refers to several moieties, including fibrin monomer, fibrin/fibrinogen dimer and fibrin oligomers. In the present application the term soluble fibrin is taken to encompass all of these soluble forms of fibrin.

Immunity and Cancer

A variety of clinical and pathologic evidence such as the presence of mononuclear cell infiltrates, composed of T-cells (Kuzushima et al., 1999), NK cells (Hokland et al., 1999), macrophages (Takanami et al., 1999) and polymorphonuclear neutrophils (PMN) (Ishikawa et al., 1986) in many tumors indicate that tumors can stimulate immune responses. Further evidence is provided by the observation of lymphocyte proliferation (hyperplasia) in lymph nodes draining sites of tumor growth (Vetto et al., 1997). In many tumors, there is evidence of cytokine effects, such as increased expression of class II major histocompatibility complex (MHC) molecules (Sikorska et al., 1999) and intercellular adhesion molecule-1 (ICAM-1; CD54) (Terol et al., 1998), suggesting an active immune response at the tumor site The spontaneous regression of tumors such as melanoma (Halliday et al., 1995) and renal cell carcinoma (Jantzer & Schendel, 1998), which are associated with dense peri- and intra-tumor lymphocytic infiltrates, is also suggestive of an immune mediated anti-tumor response.

In the blood, tumor cells encounter effector cells of the immune system, all of which are capable of anti-tumor activity, under appropriate conditions, using a variety of effector mechanisms. The most potent of these cells in the blood is considered to be the natural killer, or NK cell (Hanna & Fidler, 1980), although other cells such as T-cells (Clark et al., 1988), monocytes (Tagliabue et al., 1979) and polymorphonuclear neutrophils (Kindzelskii & Petty, 1999) show considerable anti-tumor cell activity after appropriate stimulation with cytokines or tumor cell products. Depletion of NK cells results in increased metastasis in experimental and spontaneous tumor models (Hanna, 1985). Activation of leukocytes by a variety of agents can induce increased tumoricidal activity. For example interleukin-2 (IL2) augments cytotoxicity by T-cells and NK cells (Maghazachi et al., 1988) (IL2 and IL2-activated leukocytes (LAK cells)) have been used as the basis for adoptive immunotherapy in cancer), mitogens such as phytohaemagglutinin enhance T-cell responses (Nouri et al., 1993) and bacterial lipopolysaccharide (Kildahl-Anderson & Nissen-Meyer, 1984) and interleukin-1 activate monocytes (Onozaki et al., 1985).

Most mononuclear leukocytes need to adhere to tumor cells for recognition and cytotoxicity to occur. There are a considerable number of adhesion and signaling molecules, as well as cytokines that modulate the interactions of leukocytes, platelets, tumor cells etc. with endothelium. The adhesion molecules that can mediate leukocyte cell adhesion include the leukocyte $\beta 2$ integrins, LFA-1 ($\alpha_L\beta 2$; CD11a/CD18) and Mac-1 ($\alpha_M\beta 2$; CD11b/CD18) which bind to ICAM-1 (and ICAM-2) on the tumor cell (Patarroyo & Makgoba, 1989). The $\beta 2$ integrins were first identified using monoclonal antibodies that inhibited lymphocyte cytotoxicity. On tumor cells which do not express ICAM-1 (many melanoma cells from fresh tumors express ICAM-1, but to very different levels (Passlick et al., 1996), other adhesion processes such as MHC class 1 and 11/T-cell receptor (Passlick et al., 1996), and the $\beta 1$ (VLA) (Schadendorf et al., 1995, 1993) and $\beta 3$ integrins (Liapis et al., 1997), which have also been implicated in tumor progression and metastasis, may become more prominent. In addition to adhesion, integrins also deliver stimulatory signals to cells involving tyrosine phosphorylation (Parsons, 1996) of various substrates, inositol lipid turnover (Rey-Ladino et al., 1999) and elevated levels of cytoplasmic calcium (Weismann et al., 1997). The consequences of integrin mediated signaling vary with the cell type, and include cell contraction, secretion, metabolism, cell proliferation and cell death.

Soluble Fibrin and Immunity in Cancer

Having cleaved fibrinogen, thrombin can remain bound to the formed fibrin (Hsieh, 1997) which protects it from degradation by its natural inhibitor, antithrombin. Thrombin inhibitors such as hirudin also have anti-metastatic effects (Esumi et al., 1991), possibly because thrombin can bind to tumor cells via specific receptors (Nierodzik et al., 1996) and increase their metastatic activity (Nierodzik et al., 1992). This may be necessary for post-clotting events such as activation of factor XIII, but is normally limited to the site of injury. sFn-bound thrombin is also resistant to inactivation (Hogg & Jackson, 1989). Thus, in patients with cancer, elevated levels of sFn may carry active thrombin in the circulation, perhaps explaining the relative resistance to anticoagulant therapy. Given that clotting activation seems to be important in blood-borne metastasis, high levels of circulating (procoagulant) sFn may also be a marker of poor prognosis.

Endothelial cells are critically important in tissue immunoregulation and in the process of tumor metastasis (Lafrenie et al., 1992). Leukocytes bind to endothelium using specific cell adhesion mechanisms, target to and recirculate through specific organs. This process involves three main groups of adhesive mechanism; selectins (Abbassi et al., 1993; Barkalow et al., 2000; Carlos & Harlan, 1994), integrins (Carlos & Harlan, 1994; Adams et al., 1997; Beekhuisen & Van Furth, 1993) and immunoglobulins (Carreno et al., 1995). Selectins are thought to be involved in the initial rolling of leukocytes along the endothelium, after which integrin binding occurs, followed by diapedesis into the underlying tissue. The β1 and β2 integrins are important mediators of leukocyte (and dendritic cell) adherence to CD54 and VCAM on endothelial cells. Endothelial cell CD54 expression is induced by cell activation by cytokines (Nakayama et al., 2001), thrombin (Palmblad & Lerner, 1992) and during inflammation. In addition, endothelial cells express $\alpha_v\beta3$ (the vitronectin receptor) (Fu et al., 2001) which can also bind to fibrin(ogen) (Kubo et al., 2001). In addition to cell associated CD54, a soluble form of the molecule can be secreted by a variety of cells and significant plasma levels are observed in some diseases such as endometriosis, prostate cancer and melanoma (Becker et al., 1992; Fortis et al., 1995). This soluble CD54 has been reported to inhibit NK function in vitro (Becker et al., 1992), possibly by blocking the β2 integrin binding of the NK cells to tumor cells.

The use of activated, genetically modified dendritic cells (Agger & Hokland, 2000) as a form of adoptive immunotherapy is becoming increasingly popular. Reintroduction of these cells in adoptive immunotherapy protocols, as well as their predecessors, tumor infiltrating lymphocytes (TIL) (Aebersold et al., 1991) and lymphokine activated killer (LAK) (Fukui et al., 1988) cells requires their homing to the target tumors and crossing of the endothelium at those sites.

Inhibition of Fibrin(ogen) Binding to Cells by Specific Peptides

Fibrin(ogen) is a ligand for many biological molecules. On leukocytes it binds to several integrins, but primarily to mac1. Studies have been performed to identify the amino acid sequences on both molecules responsible for binding. Small peptides were derived from fibrinogen and mac1 and tested for their ability to inhibit fibrinogen binding. Several peptides have been identified, but the most inhibitory of them are considered to be the major binding sites.

On mac1 a sequence on the αM I-domain, [245]KFGDPLGYEDVIPEADR[261] (SEQ ID NO: 1; Yakubenko et al., 2001) and its complementary peptide on the fibrinogen γ-chain, [377]YSMKKTTMKIIPFNRLTIG[395] (SEQ ID NO: 2; Ugarova et al., 1998) have been identified. Similarly, sequences on the ICAM-1 1st Immunoglobulin domain ([8]KVILPRGGSVLVTC[21] SEQ ID NO: 3; D'Souza et al., 1996) responsible for binding to the fibrinogen .gamma.-chain ([117]NQKIVNLKEKVAQLEA[133] SEQ ID NO: 4; Altieri et al., 1995) are among the most potent inhibitors of fibrin(ogen) binding. ICAM-1 is expressed by many cell types including activated endothelial cells, leukocytes and many cancers. In order for fibrin(ogen) to bind to cells it must first undergo a conformational change to expose these sites which may occur when fibrinogen is immobilized on endothelial cells.

It has been demonstrated that plasma soluble fibrinogen does not adhere. Fibrin(ogen) binding to endothelial cells has been reported to enhance monocyte adherence and it is proposed that this may augment the immune response to inflammatory sites. However, no consideration is given to the elevated plasma levels of soluble fibrin (which is likely to be conformationally altered) in the blood of patients with cancer and many other conditions. In patients having elevated levels of sFn, both adherent cell types will become coated with sFn resulting in a profound inhibition of binding, characterized by an ongoing immunosuppression in these diseases, rather than the current hypothesis of enhancement of the immune response.

Soluble Fibrin in Other Diseases

In addition to cancer and metastasis, soluble fibrin is increased in a wide range of other diseases, and has been correlated with prognosis in several of them. These diseases include: nephritic syndrome (Iioka et al., 1984), diabetes mellitus (Smolenskij et al., 1979), pancreatitis (Gubergrits et al., 1993), pregnancy complications (Ostlulnd et al., 1998), coronary artery disease (Hetland et al., 2002), acute inflammation and infarction (Lindahl et al., 1990), liver disease (vanDe Water et al., 1986), myocardial infarction (Nowak et al., 1972), disseminated intravascular coagulation (DIC; Wada et al., 2003), pulmonary embolism (Bynum et al., 1976), leukemia (Zhao et al., 2000), arthritis (Koga, 2004), sepsis (Selim et al., 2005), atherosclerosis (Wang, 1996) etc. Little or no research has been performed to determine the role of soluble fibrin in the etiology of these diseases.

Thus, the prior art is deficient in an understanding the role of soluble fibrin in the etiology of cancer, cardiovascular disease, arthritis and inflammation. Additionally, there is a lack of knowledge in the prior art of therapeutic agents that can be used to treat diseases having elevated levels of soluble fibrin. The present invention fulfills this long-standing need and desire in the art.

SUMMARY OF THE INVENTION

In one embodiment of the present invention, there is provided an isolated peptide. Such an isolated peptide may comprise one or more cell-binding domains in a soluble fibrin protein or fragments of the domain or derivatives of the domain. It may also comprise one or more soluble fibrin protein binding domains in a cell or fragments of the domains or derivatives of the domain.

In a related embodiment of the present invention, there is provided a recombinant peptide comprising the amino acid sequence of the peptide described supra.

In yet another related embodiment of the present invention, there is provided a pharmaceutical composition comprising the peptide described supra or the recombinant peptide described supra and a pharmaceutically acceptable carrier.

In another related embodiment of the present invention, there is provided a method of treating an individual diagnosed with a disease associated with increased amounts of soluble fibrin. This method comprises administering pharmacologically effective amounts of the pharmaceutical composition described supra to the individual, thus treating the individual diagnosed with the disease.

In yet another related embodiment of the present invention, there is provided a method of treating an individual diagnosed with a cancer. Such a method comprises administering pharmacologically effective amounts of the pharmaceutical composition described supra to the individual. Such an administration reduces inhibition of cell adherence, restores immune response, inhibits progression of solid tumor or a combination thereof in the individual, thus treating the individual diagnosed with the cancer.

In still yet another related embodiment of the present invention, there is provided a method of treating an individual diagnosed with a metastatic cancer. This method comprises administering pharmacologically effective amounts of the pharmaceutical composition described supra to the individual. Such an administration reduces inhibition of cell adherence due to the soluble fibrin, restores immune response, inhibits enhancement of metastasis or a combination thereof in the individual, thus treating the individual diagnosed with the metastatic cancer.

In another related embodiment of the present invention, there is provided a method of reducing soluble fibrin protein-induced immunosuppression in an individual. This method comprises administering pharmacologically effective amounts of the pharmaceutical composition described supra to the individual. Such an administration restores binding of the immune cells to tumor cells, restores immune response or a combination thereof in the individual, thus reducing the soluble fibrin protein-induced immunosuppression in the individual.

BRIEF DESCRIPTION OF THE DRAWINGS

FIG. 7A shows adherence of monocytes to soluble fibrin treated tumor cells and FIG. 7B shows adherence of monocytes to untreated tumor cells.

FIG. 8A shows the effect of peptide 1 and 2 and FIG. 8B show effect of peptide 3 and 4 on soluble fibrin inhibition of monocyte adherence to A375 melanoma cells.

FIG. 10 shows the effect of perfusion flow rate on monocyte adherence to tumor cells. Monocytes ($1\times10^6$/ml) were perfused across a monolayer of A375 cells attached to a coverslip in a perfusion stage incubator for 1 h at 370 C, and non-adherent cells were washed off by perfusion to waste for 10 min. Monocyte adherence was maximal at a flow rate of 0.5 ml/min, and linearly decreased as the flow rate was increased to 1, 1.5, and 2 ml/min.

FIGS. 11A-11B show the effect of sFN on the adherence of monocytes to tumor cells using fluorescent dyes. Tumor cells were grown on 40 mm coverslips to confluence and labeled with Calcein AM (green). Monocytes were labeled with DiI (C18; red), made to 1×106 cells/ml and continuously perfused across the tumor cells at 0.5 ml/min for 1 h.

FIG. 11A shows monocyte adherence to untreated A375 cells. FIG. 11B shows monocyte (pre-treated with sFn) adherence to sFn pre-treated A375 cells. sFn pre-treatment of both effector and target cells inhibited monocyte adherence.

FIG. 12 shows effect of monoclonal anti-$\alpha_L\beta2$, -$\alpha_M\beta2$ and CD54 on monocyte adherence to tumor cells under flow conditions in the presence or absence of sFn. Anti-$\alpha_L\beta2$ inhibited monocyte adherence to untreated cells (P<0.05; n=3), but was significantly (P<0.01 compared to non-sFn treated cells; n=3) less effective in blocking monocyte binding to sFn pre-treated tumor cells. Conversely, anti-$\alpha_M\beta2$ inhibited monocyte adherence to sFn pre-treated tumor cells to a significantly (P<0.01) greater extent than to untreated tumor cells. Anti-CD54 inhibited monocyte adherence to untreated tumor cells by over 50%, and by over 80% when tumor cells were preincubated with sFn. Isotypic control IgGs or an irrelevant monoclonal antibody (CD4) did not affect monocyte adherence.

FIG. 13 shows effect of specific blocking peptides designated P1 (binds to CD54) and P2 (binds to $\alpha_M\beta2$) on sFn inhibition of monocyte/tumor cell adherence under flow conditions. (from left to right): sFn pre-treatment of monocytes and A375 cells (n=25) significantly (P<0.01 compared to untreated control; n=30) inhibited monocyte adherence. Pretreatment of cells with P1 and P2 restored cell adherence to levels not significantly different to that of the untreated control (P<0.05 to fibrin (n=10); P>0.05 to control). Pretreatment of tumor cells with P1 and monocytes with sFn or tumor cells with sFn and monocytes with P2 inhibited adherence to a similar level to that of sFn treatment of both cells (P>0.05 to fibrin; n=5 in each case). Pretreatment of effector and tumor cells with fibrinogen (Fg), thrombin or GPRP did not significantly inhibit adherence (P>0.05 compared to untreated cells; n=5).

FIG. 14 shows effect of specific blocking peptides designated P3 (binds CD54 binding site on sFn) and P4 (binds to £\M£]2 binding site on sFn) on sFn inhibition of monocyte/tumor cell adherence under flow conditions. (from left to right): sFn treatment of monocytes and A375 cells (n=25) significantly (P<0.01 compared to untreated control; n=10) inhibited cell adherence. Pretreatment of sFn with P3 and P4 restored cell adherence to levels not significantly different to the untreated control (P<0.05 to fibrin; n=5; P>0.05 to control). Pre-treatment of tumor cells and/or monocytes with either P3+P4, P3 alone or P4 alone were not inhibitory (P>0.05; n=5 in each case, compared to untreated control).

FIGS. 15A-15F show effect of $\alpha_M\beta2$ and CD54 specific blocking peptides in sFn adherence to monocytes and tumor cells. Oregon Green labeled fibrinogen (0.5 mg/ml; Molecular Probes, Eugene, Oreg.) was treated with thrombin (1.25 U) in the presence of 4 mM GPRP-NH2 to produce fluorescently labeled sFn. A375 cells were incubated with labeled sFn for 20 min in a Bioptechs FCS2 enclosed stage incubator. The residual sFn was washed away by perfusion and the cells were imaged on an Olympus BX61 fluorescence microscope equipped with a long pass 535 nm dichroic filter. Considerable binding of sFn was observed. FIG. 15A is a representative image showing tumor cell sFn binding. In contrast, little or no binding was observed when cells were preincubated with peptides P1+P2 (FIG. 15B), or sFn with P3+P4 (FIG. 15C). Similarly, sFn bound readily to monocytes (FIG. 15D), but was inhibited when cells were pre incubated with P1+P2 (FIG. 15E), or sFn was pre-treated with P3+P4 (FIG. 15F).

FIG. 16A shows that $\alpha_L\mu2$ (orange) binds preferentially compared with $\alpha_M\beta2$ (blue) to tumor cell CD54. FIG. 16B shows that pre-treatment of tumor cells with sFn inhibits $\alpha_L\beta2$ ($\alpha_L\beta2$ does not bind fibrin(ogen) binding, but enhances $\alpha_M\beta2$ mediated adherence). FIG. 16C shows that pre-treatment of monocytes with sFn (sFn binds to $\alpha_M\beta2$) allows adherence by both $\alpha_L\beta2$ and sFn bound $\alpha_M\beta2$ to tumor cell CD54. FIG. 16D shows that pre-incubation of monocytes and tumor cells with sFn inhibits both $\alpha_L\beta2$ and $\alpha_M\beta2$ binding to sFn coated CD54.

DETAILED DESCRIPTION OF THE INVENTION

Figure 1:
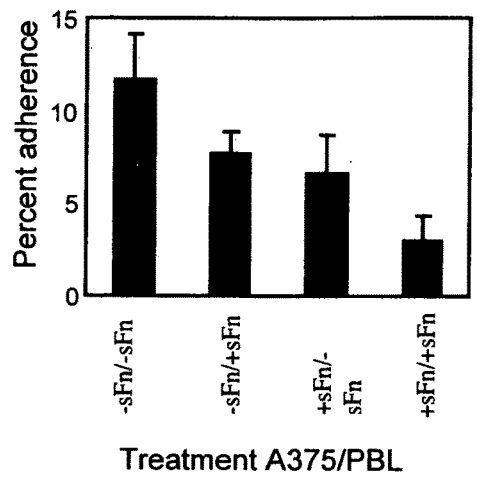
FIG. 1 shows the effect of pre-treatment of tumor cells and peripheral blood leukocytes (PBL) with soluble fibrin (sFn) on lymphocyte adherence to tumor cells. Calcein labeled peripheral blood leukocytes were incubated with A375 cells after pre-treatment of A375 and/or peripheral blood leukocytes with RPMI or sFns prior to assay. sFn pre-treatment of either cell-type alone resulted in decreased adherence (P<0.05). Maximal inhibition occurred when both cell types were treated with sFn (P<0.05) compared to single treatment.

Generally, cells of the immune system are capable of identifying and killing cancer cells. However, in many cancer patients the immune system is compromised, thereby making it difficult to efficiently eradicate invasive tumor cells from the tissues and blood. The reason for this is only partially understood. It has been reported that fibrin, the end product of blood coagulation may contribute to the inhibition of immune response against cancer by physically blocking cell contact and hence inhibiting recognition and killing.

However, the present invention explored the possibility that fibrin may inhibit immune response by masking specific receptors on both tumor cells and leukocytes. In order to accomplish this, a form of fibrin called soluble fibrin, which occurred in the blood of many cancer patients as well as individuals with cardiovascular diseases, arthritis, inflammatory bowel disease and inflammation was investigated. Since soluble fibrin could bind to $\alpha IIb\beta3$, $\alpha_M\beta2$, $\alpha4\beta1$, cell surface and soluble CD54 and $\alpha v\beta3$; was highly elevated in the plasma of many cancer patients; cross-linked platelets to tumor cells; inhibited leukocyte adherence and cytotoxicity against tumor cells and increased experimental metastasis, it was hypothesized that soluble fibrin was a major etiological agent in blood borne metastasis, and might also inhibit the cytotoxic activity of leukocytes homing to tumors.

Several clinical studies had reported that treatment of cancer patients with anti-coagulants (which stop fibrin formation) in addition to regular anti-cancer therapies was effective in reducing metastasis. However, inhibition of blood coagulation resulted in an increased tendency to bleed from wounds, tumors and surgical incisions, thereby subjecting the patient to a greater risk. Therefore, an alternative mechanism by which fibrin enhancement of metastasis could be inhibited by blocking the immune binding sites of the fibrin molecule and those of its cellular receptors without inhibiting blood coagulation was investigated. Previous studies had also indicated that immobilized fibrinogen undergoes a conformational change that allowed it to bind to activated endothelial cells and cross-link blood monocytes, thereby enhancing adherence. This was thought to be a mechanism for enhanced recruitment of leukocytes to sites of inflammation since unbound blood fibrinogen was not conformationally altered and did not bind leukocytes. However, despite the fact that soluble fibrin was elevated in many cancer patients and in over 95% of those undergoing metastasis, none of the studies took into account presence of soluble fibrin in the blood to contribute to inhibition of immune response.

Previous studies had showed that soluble fibrin enhanced platelet adherence to tumor cells and tumor metastasis in an experimental model. Furthermore, soluble fibrin also bound to the leukocyte integrin receptor, CD54 and inhibited leukocyte attachment and killing of tumor cells. This immunosuppression could also enhance metastasis since circulating tumor cells will be protected from immune attack in the blood. The present invention demonstrated a pronounced inhibition of cell adherence when both leukocytes and tumor cells (which constitutively express CD54 as activated endothelial cells) were treated with soluble fibrin. Thus, when soluble fibrin is elevated in blood, both leukocytes and endothelial cells (or tumor cells undergoing metastasis) will be coated with fibrin, resulting in inhibition of adherence and consequently homing of the leukocytes to the sites of inflammation. The tumor cells used herein are malignant melanoma cells since they are aggressively metastatic cancer and have been the focus of much clinical trials of immunotherapeutic agents. However, any circulating tumor cells expressing these common adherence molecules will also be subject to the action of soluble fibrin. Hence, soluble fibrin is a general enhancer of metastasis and an immunosuppressant in cancer.

In addition to the work presented herein, the role of soluble fibrin in tumor cell interactions with blood cells at the endothelium where metastasis occurs is investigated. It is important for tumor cells to extravasate in order to gain access to the secondary tissue. Platelet/tumor cell adherence (enhanced by sFn) increases metastasis, possibly by additional platelet/endothelial adherence, or by increased availability of vascular permeability factors from platelets and tumor cells. Blocking of CD54 on endothelial cells by sFn may inhibit leukocyte adherence, recirculation and targeting to tumors in tissues. Furthermore, coating of potentially cytotoxic immunotherapeutic leukocytes (LAK cells, TILs modified dendritic macrophages etc.) by sFn after reintroduction into the circulation may significantly impair their ability to extravasate and target to the tumors in vivo. This may seriously reduce the efficacy of these emerging therapies.

Although previous studies had identified the mechanism of fibrinogen binding by blocking its adherence to monocytes and endothelial cells using specific peptides, no consideration was given to the biological activities of soluble fibrin in the planning of these therapeutic protocols. The present invention demonstrated that the peptides used to block fibrinogen adherence could also inhibit soluble fibrin from binding to blood monocytes and tumor cells and thus restoring monocyte adherence and cytotoxicity against tumor cells.

sFn coated tumor cells were shown previously to enhance metastasis in an experimental metastasis model (Biggerstaff et al., 1999). Further studies using monoclonal blocking antibodies showed that sFn bound to the β2 integrin receptor, CD54, which was present on many cancer cells. Other reports have demonstrated that fibrinogen binds to $\alpha_M\beta2$ on leukocytes [Ugarova et al., 1998; Yakovlev et al., 2005).

Figure 9:
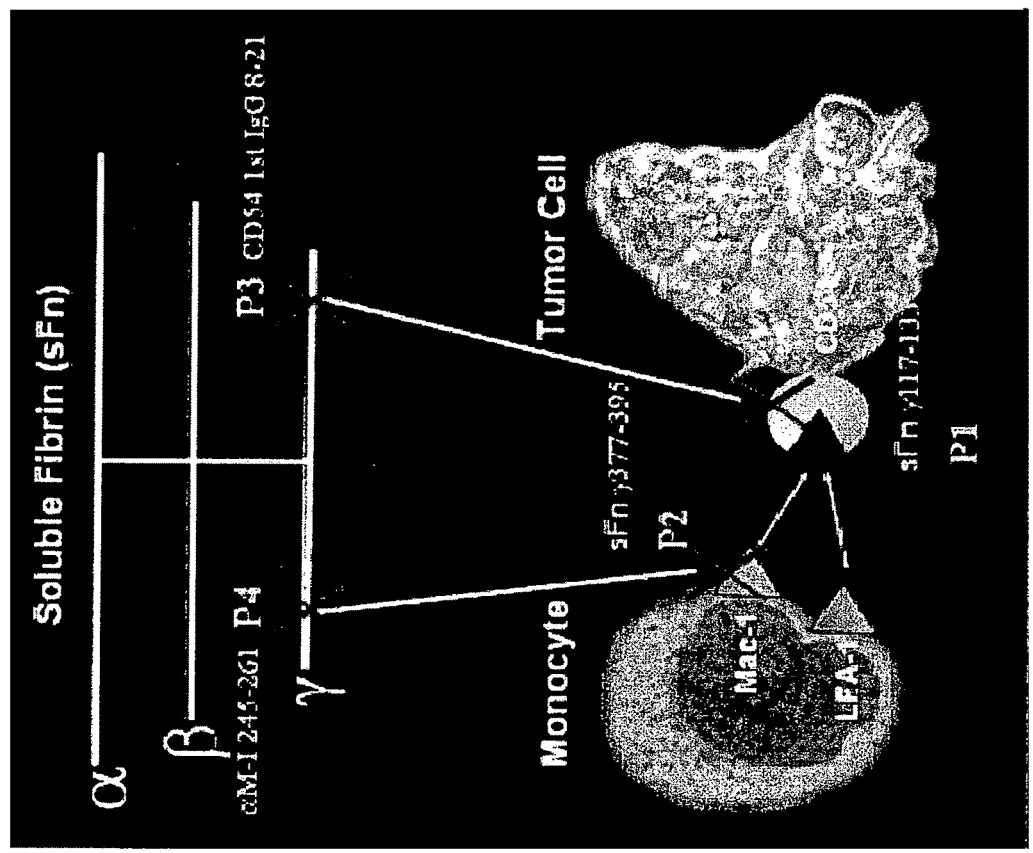
FIG. 9 is a schematic representation of the amino acid sequences, sites of origin and effector molecules for four peptides (designated P1-P4) reported to inhibit fibrin(ogen) binding to $\alpha_M\beta2$ (orange) and CD54 (blue).
Figures 16A, 16B, 16C, 16D:
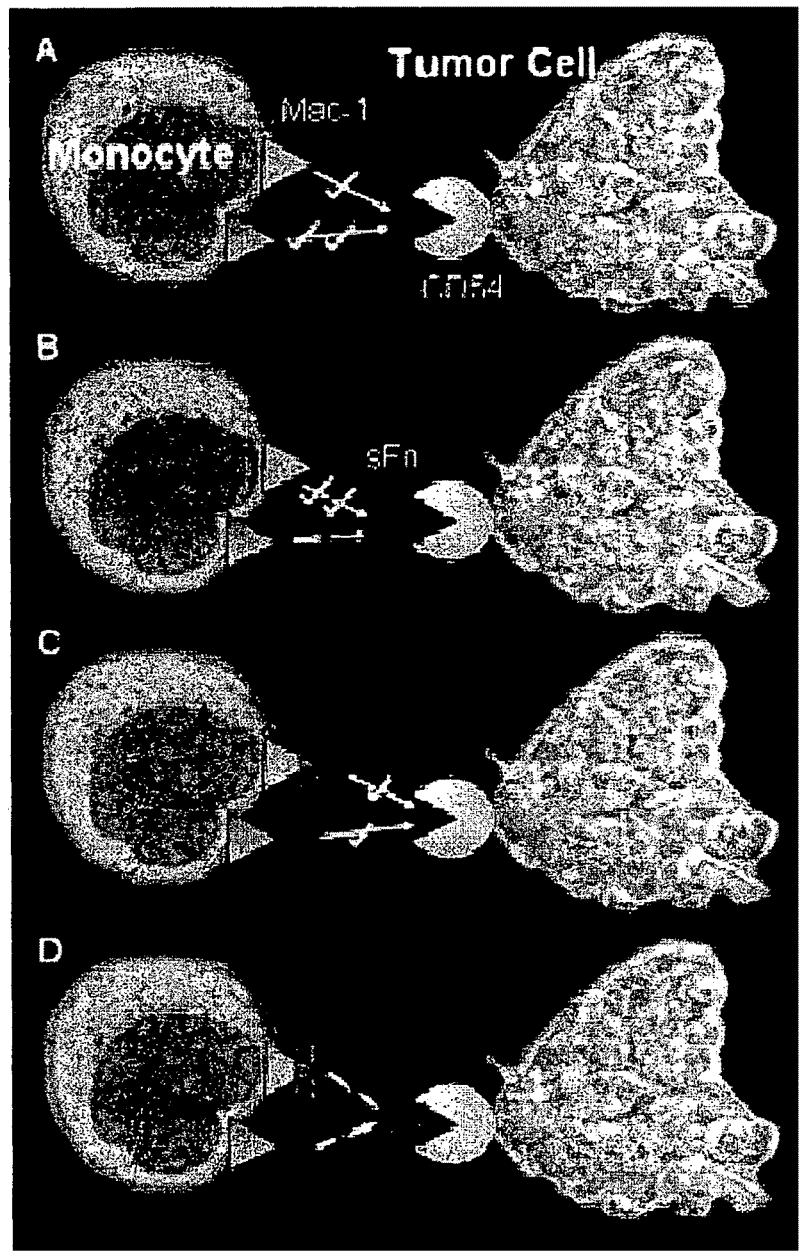
FIGS. 16A-16D are schematic diagrams summarizing the proposed mechanism of sFn mediated inhibition of monocyte adherence (and consequently cytotoxicity) to tumor cells.

The microplate monocyte/tumor cell adherence assays discussed herein demonstrated adherence of monocytes to tumor cells (FIG. 9). Pre-treatment of tumor cells with sFn considerably enhanced monocyte binding. This result was consistent with the report by Ugarova et al., 1998 that showed increased monocyte binding to fibrinogen bound endothelial cells. Indeed, this has been postulated as a mechanism of increased immune cell homing to inflammatory sites. A small, but non-significant increase in monocyte adherence was also observed when monocytes were pre-incubated with sFn. However, monocyte adherence was inhibited by over fifty percent when both cell types were sFn treated prior to assay. Since sFn levels are elevated in many cancer patients, peripheral blood monocytes and circulating tumor cells undergoing metastasis would likely be coated in sFn, thereby reducing their ability to adhere to each other.

Figure 5:
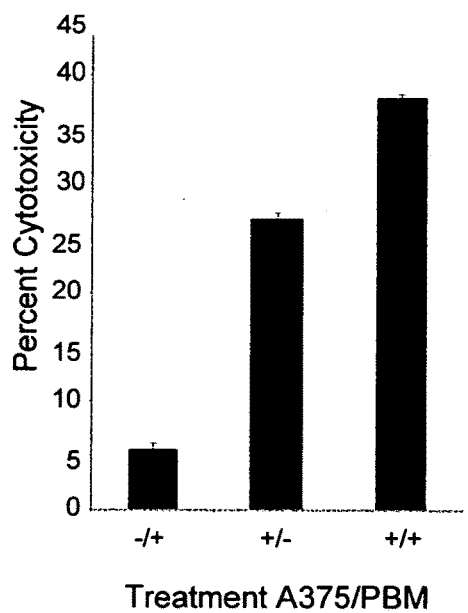
FIG. 5 shows the effect of sFn pre-treatment on monocyte cytotoxicity against tumor cells. Calcein AM labeled PBM incubated with A375 cells after pre-treatment of A375 with or without sFn and pretreatment of PBM with or without sFn prior to assay. sFn pre-treatment of monocytes was slightly inhibitory (P<0.05 compared to untreated control; n=3). Significantly greater inhibition was observed when A375 cells were sFn pre-treated (P<0.01 compared to untreated and to monocyte treated cells; n=3). Maximal inhibition of PBM cytotoxic activity occurred when both cell types were treated with sFn (P<0.01 compared to untreated, monocyte treated or A375 treated cells: n=3).
Figure 6:
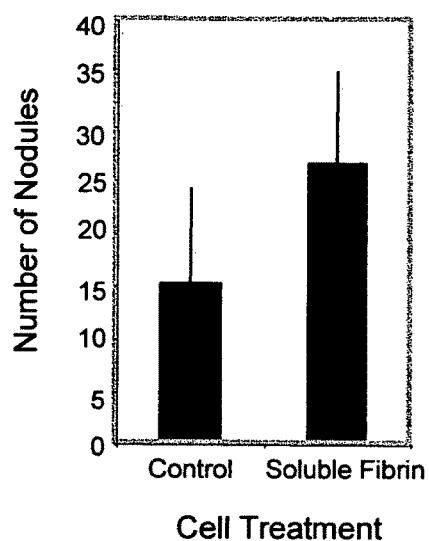
FIG. 6 shows the effect of soluble fibrin in vivo. Injection of sFn pre-treated LL2 cells significantly (P<0.05) increased lung metastasis compared to untreated tumor cells (26.6±8.7 vs 15.2±9.1, respectively).

Since adherence is a necessary step in most cytotoxic effector pathways, cellular cytotoxicity assays were performed to determine if monocyte killing of tumor cells was similarly inhibited by sFn When both cell types were untreated, specific monocyte cytotoxicity was 28.6+0.7 (FIG. 5). A small, but non significant (P>0.05) inhibition was observed when monocytes were sFn pre-treated. However, a greater inhibition (P<0.05 compared to untreated cells) was observed when untreated monocytes were incubated with sFn treated tumor cells. This was interesting, since increased monocyte adherence was observed under similar conditions (FIG. 9). This suggested that although sFn bound to tumor cells increased monocyte adherence, it might inhibit subsequent signaling to allow delivery of the cytotoxic lethal hit to the tumor cells.

Furthermore, these results were consistent with the previously published data showing increased metastasis when sFn treated tumor cells were injected into warfarinized mice (Biggerstaff et al., 1999). SFn pretreatment of both monocytes and tumor cells resulted in the greatest inhibition of cytotoxicity (P<0.05 compared to both untreated and sFn treated tumor cells), which was consistent with the observed decrease in adherence under similar conditions. Taken together, these results suggested that, in vivo, elevated levels of circulating sFn would result in its binding to both tumor cells and monocytes, leading to an ongoing immunosuppression as discussed herein.

To investigate the mechanism of sFn inhibition, monoclonal blocking antibodies directed against monocyte $\alpha_L\beta2$ and $\alpha_M\beta2$, or tumor cell CD54 were incubated with untreated or sFn treated monocytes and tumor cells (FIG. 12). Pre-incubation of monocytes with blocking anti-$\alpha_L\beta2$ inhibited adherence to tumor cells by over eighty percent. However, inhibition by anti-$\alpha_L\beta2$ was significantly (P<0.01) reduced when tumor cells were sFn treated. Conversely, monocyte pretreatment with blocking anti-$\alpha_M\beta2$ had relatively little effect on adherence to untreated tumor cells, but significant blocking was observed if the tumor cells were sFn treated. Although this antibody has not been reported to block fibrin(ogen) binding to $\alpha_M\beta2$, it is likely to block the binding since the epitope for this clone is on the $\alpha_M$ I-domain, which is proximal to the fibrin(ogen) γ-chain binding site on $\alpha_M$.

These data suggested that, in the absence of sFn, unstimulated monocyte adherence was mediated predominantly via $\alpha_L\beta1$, whereas $\alpha_M\beta2$ seemed to predominate in binding to sFn treated tumor cells. This was consistent with previous observations that fibrin(ogen) binds to $\alpha_M\beta2$ (Yakovlev et al., 2005). These results were further supported by the observation that pre-treatment of tumor cells with blocking anti-CD54 inhibited untreated monocyte adherence and was even more effective in blocking adherence of sFn treated monocytes. This observation was supported by the observations of Gardiner and D'Souza, 1997. This clone of anti-CD54 (84H10) inhibited both β2 integrin and fibrinogen binding to CD54. Isotypic murine immunoglobulin isotype or an irrelevant monoclonal antibody (anti-CD4) had no effect on monocyte-tumor cell adherence in the presence or absence of sFn.

To further investigate the mechanism of sFn inhibition of monocyte/tumor cells adherence, four peptides were chosen which had previously been reported to represent major fibrin(ogen) binding sites on CD54 (P1) and $\alpha_M\beta2$ (P2) for fibrin(ogen), and the fibrin(ogen) γ-chain binding sites for CD54 (P3) or $\alpha_M\beta2$ (P4). Blocking of the fibrin(ogen)

binding sites on both monocytes ($\alpha_M\beta2$) and tumor cells (CD54), prior to sFn treatment significantly (P<0.05) reduced sFn mediated inhibition of monocyte/tumor cell adherence under flow conditions (FIG. 13). Blocking of both the CD54 and $\alpha_M\beta2$ binding sites on sFn again significantly (p<0.05) reduced the ability of sFn to inhibit monocyte adherence (FIG. 14).

In further experiments Oregon Green-labeled sFn was incubated with tumor cells or monocytes alone or after appropriate cell or sFn blocking peptide treatment. Fluorescence microscopy (using exactly the same microscope settings for all slides) showed a considerable reduction in sFn binding to either cell type after appropriate cell or sFn treatment with either P1+P2, or P3+P4, confirming that peptide treatment inhibited sFn binding to the cells (FIG. 15A-15F). Further evidence of the specificity of the blocking peptides was provided in experiments demonstrating their inability to inhibit normal fibrinogen clotting in a pure system and in recalcified plasma.

The results discussed herein are summarized in FIG. 16A-16D. Briefly, the presence of sFn on tumor cells enhanced monocyte binding, probably by upregulating $\alpha_M\beta2$ binding to sFn coated CD54 (FIG. 16B). Pre-treatment of monocytes (but not tumor cells) with sFn did not affect monocyte adherence, probably because free tumor cell CD54 was still available to bind monocyte $\alpha_L\beta2$ (FIG. 16C). Pretreatment of both cells with sFn inhibited both $\alpha_M\beta2$ and $\alpha_L\beta2$ mediated adherence (FIG. 16D), which was the most likely situation in vivo, in patients with elevated levels of circulating sFn. Extrapolation of these results to the physiological setting would suggest that, in cancer patients with elevated levels of sFn, monocytes and circulating tumor cells would bind sFn, resulting in the inability of monocytes to adhere to, and kill, tumor cells, resulting in enhanced metastasis. Hence, the use of fibrin blocking peptides may represent a novel class of therapeutic agents to reduce sFn mediated immunosuppression, and decrease metastasis in many cancers, while avoiding the negative bleeding problems commonly associated with anticoagulant therapies. The principle discussed herein might also be effective in a variety of other disease conditions. Hence, it is contemplated that these peptides and any of the derivatively effective analogues could be used as potential therapeutic agents in cancer progression and metastasis as well as in cardiovascular disease and other diseases in which fibrin and soluble fibrin were present.

The present inventions is directed to an isolated peptide, comprising: one or more cell-binding domains in a soluble fibrin protein or fragments of said domains; or one or more soluble fibrin protein binding domains in a cell or fragments of said domains. Additionally, the peptides may have amino acid sequences that are at least 80% or 90% homologous to the cell-binding regions in the soluble fibrin or to the soluble fibrin-binding regions in the cell. Representative examples of the peptides that comprise the cell-binding region on the soluble fibrin may include but are not limited to SEQ ID NO: 5, (SEQ ID NO: 6) or fragments of the domain or derivatives of the domain, and those that comprise the soluble fibrin-binding region in the cell may include but are not limited to SEQ ID NO: 3, SEQ ID NO: 7 or fragments of the domain or derivatives of the domain. Furthermore, the cell whose binding to soluble fibrin is blocked in such a method may include but is not limited to an immune cell, an endothelial cell or a tumor cell.

The present invention is also directed to a recombinant protein comprising an amino acid sequence of the isolated peptide described supra and to a pharmaceutical composition comprising the peptide or the recombinant peptide described herein and a pharmaceutically acceptable carrier.

The present invention is further directed to a method of treating an individual diagnosed with a disease associated with increased amounts of soluble fibrin, comprising administering pharmacologically effective amounts of the pharmaceutical composition described herein to the individual, thereby treating the individual diagnosed with the disease. Such a method may further comprise administering an immunotherapeutic agent, a cytotoxic drug or a chemotherapeutic agent. The immunotherapeutic agent, the cytotoxic drug or the chemotherapeutic agent may be administered concurrent with, subsequent to or sequential to the above-discussed composition. Additionally, the composition administered herein reduces inhibition of cell adherence, induction of immunosuppression, enhancement of blood-borne or lymphatic metastasis, protection of cancer cells in the primary or secondary solid tumor from immune attack, progression of solid tumor growth or a combination thereof. Examples of diseases that can benefit from this method may include but are not limited to cancer, nephritic syndrome, diabetes mellitus, pancreatitis, pregnancy complications, coronary artery disease, acute inflammation and infarction, liver disease, myocardial infarction, disseminated intravascular coagulation, pulmonary embolism, arthritis, sepsis or atherosclerosis. Examples of types of cancer that can benefit from this method may include but are not limited to leukemia, melanoma, renal cell carcinoma, small cell lung cancer, prostate cancer, breast cancer or any cancer where the cancer cell binds to soluble fibrin.

The present invention is further directed to a method of treating an individual diagnosed with a cancer, comprising: administering pharmacologically effective amounts of the pharmaceutical composition described supra to the individual, where the administration reduces inhibition of cell adherence due to the soluble fibrin, restores immune response, inhibits progression of solid tumor or a combination thereof in the individual, thereby treating the individual diagnosed with the cancer. Such a method may further comprise administration of an anticancer agent. The anticancer agent may be administered concurrent with, subsequent to or sequential to the above-discussed composition. The cancer that can be treated using such a method may include but is not limited to melanoma, leukemia, renal cell carcinoma, small cell lung cancer, prostate cancer, breast cancer or any cancer where the cancer binds to soluble fibrin.

The present invention is still further directed to a method of treating an individual diagnosed with a metastatic cancer, comprising: administering pharmacologically effective amounts of the pharmaceutical composition described supra to the individual, where the administration reduces inhibition of cell adherence due to the soluble fibrin, restores immune response, inhibits enhancement of metastasis or a combination thereof in the individual, thereby treating the individual diagnosed with the cancer. Such a method may further comprise administration of an anticancer agent. The anticancer agent may be administered concurrent with, subsequent to or sequential to the above-discussed composition. The metastatic cancer that can be treated using such a method is a blood borne or lymphatic metastatic cancer and may include but is not limited to melanoma, leukemia, renal cell carcinoma, small cell lung cancer, prostate cancer, breast cancer or any cancer where the cancer binds to soluble fibrin.

The present invention is also directed to a method of reducing soluble fibrin protein-induced immunosuppression in an individual, comprising: administering pharmacologically effective amounts of the pharmaceutical composition described supra to the individual, where the administration restores binding of the immune cells to the tumor cells, restores immune response or a combination thereof in the individual, thereby reducing the fibrin-induced immunosuppression in the individual. Such a method may further comprise administration of an immunotherapeutic agent. The immunotherapeutic agent may be administered concurrent with, subsequent to or sequential to the above-discussed composition. The individual benefiting from such a method may include but is not limited to the individual who has cancer, cardiovascular disease, arthritis or any other soluble fibrin-induced immunosuppressive disease.

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof. As used herein, the term "derivatives thereof" of the peptides that comprise the cell-binding region on soluble fibrin or of the peptides that comprise the soluble-fibrin binding region on the cell may mean those peptides whose amino acid sequence is derived from the peptides that comprise the cell-binding region on soluble fibrin or of the peptides that comprise the soluble-fibrin binding region on the cell. Such peptides may include but are not limited to those peptides that comprise at least 3 amino acids.

As used herein, the term "cell-binding domain" of a soluble fibrin protein is a structurally and/or functionally discrete region within the soluble fibrin protein that is involved in the binding of the soluble fibrin to a cell. Similarly, as used herein, the term "soluble fibrin protein binding domain" of a cell is a structurally and/or functionally discrete region within the cell that is involved in the binding of the cell to the soluble fibrin. As used herein, the term "soluble fibrin" encompasses a range of different molecular structures of fibrin during its progression to polymerization. The effects of soluble fibrin disclosed herein may also be applicable to a fibrin polymer and crosslinked fibrin polymer which are present in the extracellular matrix of many cancers and also inhibit the immune system in the same manner as the soluble fibrin. Hence, the peptides disclosed herein may also be used to reverse or reduce the effects of the fibrin polymer and crosslinked fibrin polymer. As used herein, the term "metastatic cancer" includes blood-borne metastatic cancer and lymphatic metastatic cancer.

The composition comprising the peptides disclosed herein may be administered either alone or in combination with another drug, a compound, a cytotoxic agent, an immunotherapeutic agent, an anti-cancer agent or a chemotherapeutic agent. Another drug, compound, anti-cancer agent, chemotherapeutic agent may be administered concurrently or sequentially with the composition comprising the peptides used herein. The effect of co-administration with the composition is to lower the dosage of the drug, the compound, the cytotoxic agent, the immunotherapeutic agent, the anti-cancer agent or the chemotherapeutic agent normally required that is known to have at least a minimal pharmacological or therapeutic effect against the disease that is being treated. Concomitantly, toxicity of the drug, the compound, the cytotoxic agent, the immunotherapeutic agent, the anti-cancer agent, the chemotherapeutic agent to normal cells, tissues and organs is reduced without reducing, ameliorating, eliminating or otherwise interfering with any cytotoxic, cytostatic, apoptotic or other killing or inhibitory therapeutic effect of the drug, compound, anti-cancer agent, chemotherapeutic agent. For instance, the co-administration of such peptides with either cytotoxic drugs or an immunotherapeutic agent will enhance immunotherapy and immune cell homing to tumors by blocking soluble fibrin and fibrin polymer induced immunosuppression.

The composition described herein and the drug, compound, cytotoxic agent, immunotherapeutic agent, anti-cancer agent, chemotherapeutic agent may be administered independently, either systemically or locally, by any method standard in the art, for example, subcutaneously, intravenously, parenterally, intraperitoneally, intradermally, intramuscularly, topically, enterally, rectally, nasally, buccally, vaginally or by inhalation spray, by drug pump or contained within transdermal patch or an implant. Dosage formulations of the composition described herein may comprise conventional non-toxic, physiologically or pharmaceutically acceptable carriers or vehicles suitable for the method of administration.

The composition described herein and the drug, compound, cytotoxic agent, immunotherapeutic agent, anti-cancer agent, chemotherapeutic agent may be administered independently one or more times to achieve, maintain or improve upon a therapeutic effect. It is well within the skill of an artisan to determine dosage or whether a suitable dosage of either or both of the composition and the drug, compound, cytotoxic agent, immunotherapeutic agent, anti-cancer agent or chemotherapeutic agent comprises a single administered dose or multiple administered doses. An appropriate dosage depends on the subject's health, the inhibition of negative contribution of the soluble fibrin to the disease, the route of administration and the formulation used.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

Example 1

Soluble Fibrin Mediated Immunosuppression

Figure 2:
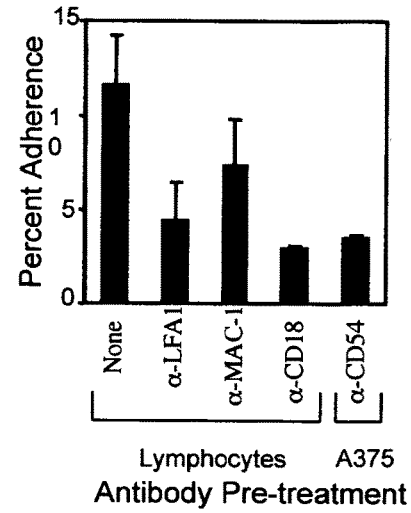
FIG. 2 shows the effect of treatment with monoclonal antibodies on the adherence of lymphocytes to tumor cells. Calcein labeled peripheral blood leukocytes were incubated with A375 cells after pre-treatment with monoclonal antibodies for 30 min prior to assay. Peripheral blood leukocytes adherence was significantly (P<0.05) reduced by preincubation of peripheral blood leukocytes with anti-LFA, anti-CD18 and to a lesser extent with anti-mac-i (possibly due to NK cells) monoclonal antibody. Pre-treatment with anti-CD54 also inhibited peripheral blood leukocytes adherence.

Soluble fibrin mediated immunosuppression was evaluated by performing leukocyte adherence and cytotoxicity assays. It was observed that lymphocyte adherence against A375 cells was inhibited by soluble fibrin pre-treatment of either cell type, and was maximal when both cells were pre-treated (FIG. 1). This suggested that soluble fibrin binds to receptors on both cells. As expected, lymphocyte adherence was significantly inhibited by incubation with anti-LFA-1, anti-CD18 and to a lesser extent by anti-mac-1 (FIG. 2). The latter was probably due to the contribution of NK cells in the lymphocyte population. NK cells express both mac-1 and LFA-1 whereas lymphocytes express only LFA-1 and are reported to be unresponsive to anti-mac1 (Timonen et al., 1988). Marked inhibition was also observed after pre-incubation of A375 cells with anti-CD54. These results indicated a primary role for the $\beta_2$ integrins in lymphocyte binding to CD54 on the tumor cells.

Figure 3:
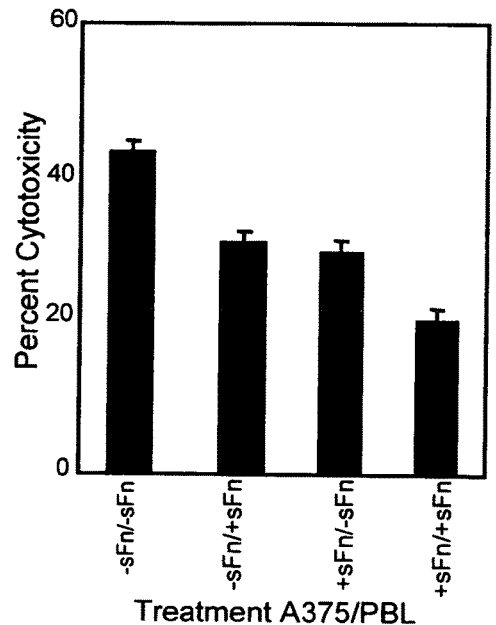
FIG. 3 shows the effect of pre-treatment with soluble fibrin on lymphocyte cytotoxicity. Calcein labeled peripheral blood leukocytes were incubated with A375 cells after pre-treatment of A375 cells with or without soluble fibrin and pre-treatment of peripheral blood leukocytes with or without soluble fibrin prior to assay. sFn pre-treatment of either cell type alone resulted in decreased cytotoxicity (P<0.05), Maximal inhibition of peripheral blood leukocytes cytotoxic activity occurred when both cell types were treated with soluble fibrin (P<0.05) compared to single treatment.

Based on the demonstration of inhibition of lymphocyte adherence by incubation of the cells with soluble fibrin, and previous demonstration that soluble fibrin binds to CD54 on the tumor cells, it was hypothesized that soluble fibrin also binds to $\beta_2$ integrins on lymphocytes and NK cells. This is supported by data showing fibrinogen binding to mac-1 (Forsyth et al., 2001). Hence, the role of soluble fibrin in LFA-1 and mac-1 mediated leukocyte subtype adherence to melanoma cells was examined. Lymphocyte cytotoxicity was also inhibited by soluble fibrin in a similar pattern to adherence, (FIG. 3) demonstrating that soluble fibrin binding to lymphocytes and tumor cells inhibits lymphocyte function in vitro.

Example 2

Figure 7A:
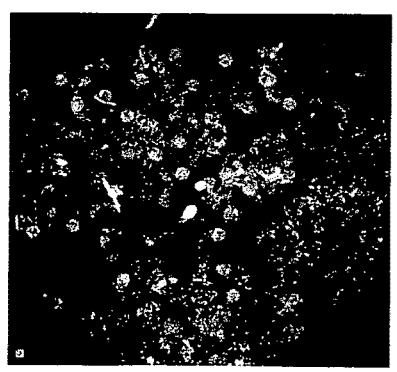
FIGS. 7A-7B show continuous perfusion of monocytes in a stage incubator. Carbocyanine dye labeled monocytes (red) were passed across adherent melanoma cells (green) for 1 h and the tumor cells were washed with tissue culture medium. The cells were then scanned using a confocal microscope. Monocytes were detected using fluorescence and tumor cells were scanned using reflectance confocal microscopy.
Figure 7B:
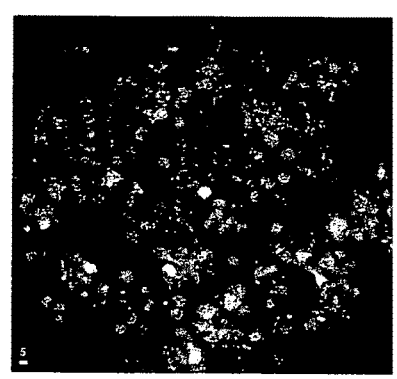

Reversal of sFn Mediated Immunosuppresion Using Specific Peptides
(a) Continuous Perfusion of Monocytes in a Stage Incubator:
Human peripheral blood monocytes, isolated by density centrifugation and adherence were labeled with the carbocyanine dye (DiI, C18; Molecular Probes, Eugene, Oreg.). They were passed across adherent soluble fibrin treated or untreated tumor cells at a shear force corresponding to that present in small blood capillaries for 1 h (FIGS. 7A and 7B).

The number of tumor cells and adherent monocytes were counted in the images and leukocyte adherence was expressed as the number of leukocytes per tumor cell. Pre-treatment of the tumor cells with soluble fibrin resulted in significantly (P<0.05) decreased monocyte binding to tumor cells. These experiments agreed with the results from the static adherence assay and demonstrated a technique to enumerate leukocyte adherence to tumor cells under flow conditions.

Figure 8B:
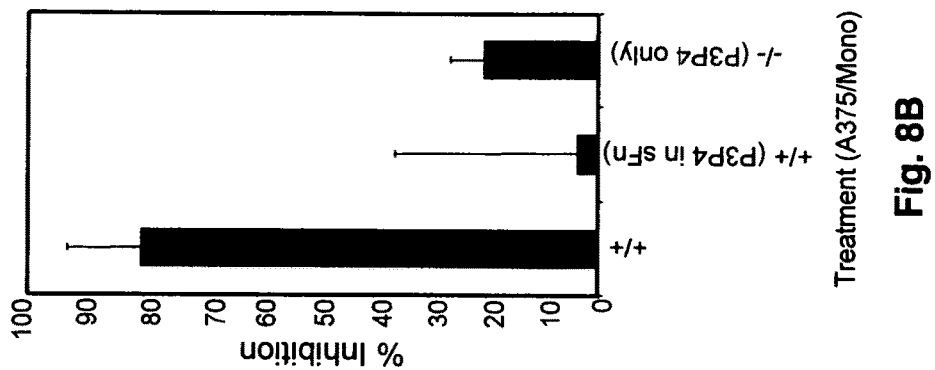
FIGS. 8A-8B show the effect of peptides on binding of monocyte to A375 melanoma cells.
Figure 8A:
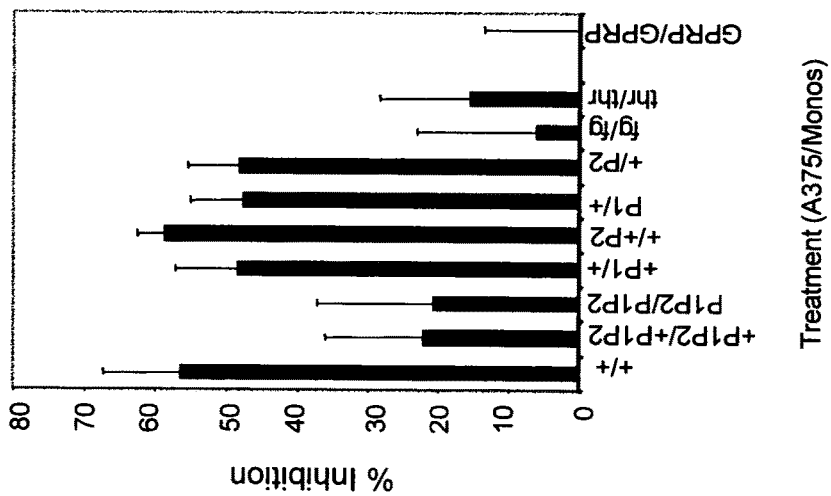

(b) Effect of Peptides on the Binding of Fibrin to the Tumor Cells:
Table 1 shows the peptides used in this study. Peptide 1 (P1) represents the fibrinogen gamma chain sequence responsible for its binding to ICAM 1. Thus, incubation of tumor cells with P1 inhibits soluble fibrin binding to tumor cells. Similarly, peptide 2 (P2) is the fibrin sequence responsible for fibrin binding to mac1. Incubation of monocytes with P2 inhibits fibrin binding to these cells. FIG. 8A shows (from left to right) that sFn pretreatment of both monocytes and tumor cells significantly inhibits adherence. Preincubation of the cells to P1 (tumor cells) and P2 (monocytes) prior to soluble fibrin incubation with both cells significantly reduces this inhibition resulting in restoration of immune cell adherence to the tumor cells at a twofold molar excess (compared to soluble fibrin).

TABLE 1

Table 1. Designation of inhibitory peptides used in this study, with molecule of origin and ligand.

| Peptide # | Sequence | Molecule of Origin | Ligand | SEQ ID NO. |
|---|---|---|---|---|
| 1 | NNQKIVNLKEKVAQLEA | soluble fibrin (g-chain) | ICAM-1 (CD54, 1$^{st}$ Ig) | 5 |
| 2 | YKSMKKTTMKIIPFNRLTIF | soluble fibrin (g-chain) | MAC1 ($\alpha_M\beta_2$, $\alpha$MI) | 6 |
| 3 | KVILPRGGSVLVTC | ICAM-1 (CD54, 1$^{st}$ Ig) | soluble fibrin (g-chain) | 3 |
| 4 | KFGDPLGYEDVIPEADREG | MAC1 ($\alpha_M\beta_2$, $\alpha$MI) | soluble fibrin (g-chain) | 7 |

Whether increasing the molar excess further reduces sFn inhibition is also determined. Incubation of cells with peptides in the absence of subsequent soluble fibrin treatment was also close to baseline adherence. Incubation of tumor cells with P1 followed by soluble fibrin treatment of both cells resulted in similar inhibition to the double soluble fibrin treatment. This was because P1 binds to ICAM1, and inhibits fibrin coated monocytes from adhering. Similarly, preincubation of monocytes with P2 prevented both fibrin binding to monocytes and blocked mac1 from binding to fibrin coated tumor cells. Similar inhibition to that of double soluble fibrin treatment was also seen if tumor cells or monocytes were incubated with P1 and P2 respectively followed by treatment of the other cell type with soluble fibrin. Rather than the enhancement of adherence (seen in FIG. 4), this marked inhibition confirmed that soluble fibrin mediated inhibition is mediated by its specific binding to ICAM1 and mac1. When cells were both treated with the individual components of the soluble fibrin mixture (i.e. fibrinogen, thrombin and the polymerization inhibitor, GPRP, little or no inhibition of adherence was observed, indicating that the end product of thrombin cleavage is required for inhibition to occur.

Peptides 3 (P3) and 4 (P4) are the complementary binding sequences on ICAM1 and mac1 for fibrin(ogen) (in this case—soluble fibrin). It was observed that preincubation of soluble fibrin with P3 and P4 almost abrogated the soluble fibrin mediated inhibition of adherence as opposed to little effect on adherence with peptides alone (FIG. 8B). These results showed that appropriate treatment of either cells (P1 and P2) or soluble fibrin itself (P3 and P4) is effective in considerably reducing the inhibition of adherence due to soluble fibrin. Based on these results, it was contemplated that these or similar peptides would restore the immune response in cancer (and possibly many other diseases) resulting in decreased metastasis and possibly be effective in enhancing the immune response in the solid tumors.

Example 3

Inhibition of Monocyte Adherence and Cytotoxicity of Tumor Cell by sFn

The role of sFn in the etiology of metastatic cancer growth has not been extensively studied. It was reported that sFn cross-linked platelet binding to tumor cells via the major platelet fibrin receptor $\alpha$IIb$\beta$3 and tumor cell CD54 (ICAM-1), which is the receptor for two of the leukocyte $\beta_2$ integrins ($\alpha_L\beta_2$ and $\alpha_M\beta_2$). Furthermore, in rat experimental metastasis model, sFn pre-treatment of tumor cells enhanced metastasis by over 60% compared to untreated cells. Other studies had shown that fibrin(ogen) binds to the monocyte integrin $\alpha_M\beta_2$. Based on this, the present invention sought to investigate the effect of sFn on β2 integrin mediated monocyte adherence and killing of tumor cells.

The role of sFn in monocyte adherence and cytotoxicity against tumor cells was initially studied using static microplate adherence and cytotoxicity assays, and under physiologically relevant flow conditions in a microscope perfusion incubator system. Blocking studies were performed using monoclonal antibodies specific for β2 integrins and CD54, and specific peptides which inhibit sFn binding to these receptors.

(a) Methods Used: Venepunture

Thirty milliliters of peripheral blood was drawn from normal, healthy volunteers into 3.2% sodium citrate vacutainers (Becton Dickinson VACUTAINER™ Systems, Rutherford, N.J.). Whole blood was diluted by adding 20 µl of blood into 180 µl 1% crystal violet stain in 0.5% acetic acid. A leukocyte count was performed in an improved Neubauer counting chamber.

Preparation of Soluble Fibrin (sFn):

sFn was made in the required amount for each experiment. To produce sFn monomer, an excess of GPRP-NH2 was added (4 mM final). To make 1 ml of sFn solution, 50 µl fibrinogen (10 mg/ml; plasminogen-, fibronectin-, and factor XIII free; American Diagnostica Inc., Greenwich, Conn.), 84 µl of the fibrin polymerization inhibitor Gly-Pro-Arg-Pro-amide (24 mM; GPRPNH2; Sigma Chemical Company), followed by 1.25 µl thrombin (100 U/ml; Sigma Chemical Company) were added to 865 µl of RPMI 1640. For experiments investigating peptide inhibition of sFn binding to monocytes and tumor cells, FITC-labeled fibrinogen (Molecular Probes, Eugene, Oreg.) was used in place of unlabeled fibrinogen discussed herein.

Culture of Tumor Cells:

The A375 human amelanotic malignant melanoma cell line was maintained in continuous cell culture. Cells were detached from plastic using trypsin/EDTA (0.25%: Hyclone, Logan, Utah) and washed in RPMI 1640 tissue culture medium containing 10% fetal bovine serum (10% FBS) centrifuged at 200×g, resuspended in 5 ml of 10% FBS, and counted.

For static adherence assays, 4×104 cells were added to the wells of a 96 well flat-bottomed microtiter plate and incubated for 24-48 or until confluent. For cytotoxicity experiments, cells were incubated with 5 µl of Calcein-AM (Molecular Probes) for 30 min, washed, counted and used at appropriate concentrations in a 96 well round-bottomed plate, to which effector cells were added. For flow experiments, the cell suspension was added to 40 mm glass coverslips together with 10% FBS in petri dishes and incubated until nearly confluent (24-48 h).

Isolation of Mononuclear Cells:

Six tubes of citrated blood were diluted 1:1 with RPMI, and 15 ml layered over 8 ml Lymphoprep™ in plastic universal containers. These discontinuous density gradients were centrifuged for 25 min at 450×g and the mononuclear cell interface removed using a sterile plastic pasteur pipette. The cells were washed three times by resuspension and recentrifugation at 200×g for 10 min in RPMI/FBS so as to remove platelets. The final cell pellets were resuspended in 10 ml RPMI. A cell count was performed by adding 20 µl of blood into 180 µl 0.5% trypan blue vital stain, and cells were counted in an improved Neubauer counting chamber.

Purification of Monocytes:

Mononuclear cells obtained from the Lymphoprep™ density gradient were adjusted to 2×106 cells/ml, and aliquots of 5×107 cells added to 75 cm2 serum coated tissue culture flasks. The flasks were incubated at 37° C., in 5% C02, for 1.5 h in order to allow monocyte adherence to the plastic. The non-adherent cells (lymphocytes) were decanted. A cell count was performed on the final cell suspension an aliquot were dried onto microscope slides for analysis of cell purity.

The flasks containing the remaining adherent cells (monocytes) were rinsed twice with RPMI and 10 ml of 3 mmol/L EDTA in RPMI/FBS added. The flasks were then incubated at 37° C. for 12 min, or until the cells have detached from the plastic (determined by observation under an inverted microscope). The cells were removed from the flasks using a 5 ml pipette, transferred into universal containers, and washed three times in 10% FBS to remove any residual EDTA. Cell purity was determined by differential counting of lymphocytes and monocytes using May-Grunwald/Giemsa stain (Sigma). It was important that the monocytes were used in experiments immediately to avoid re-adherence to the plastic, which would result in a decreased cell yield. In 19 experiments, the mean monocyte purity was 92+5%.

Preparation of Soluble Fibrin Solution:

To produce 1 mL of sFn monomer solution, 50 µl fibrinogen (10 mg/ml; plasminogen-, fibronectin-, and factor XIII free; American Diagnostica Inc., Greenwich, Conn.), 84 µl of the fibrin polymerization inhibitor Gly-Pro-Arg-Pro-amide (24 mM; GPRP-NH2; Sigma Chemical Company), followed by 1.25 µl thrombin (100 U/ml; Sigma Chemical Company) was added to 865 µl of RPMI 1640.

Cellular Adherence Assay:

Tumor cells were detached from plastic using trypsin (0.25%)/EDTA (0.1 µM) and washed in cell culture medium. Forty thousand cells (in 200 µl 10% FBS) were added to each well of a 96 well, flat bottomed tissue culture plate and incubated at 37° C. until confluent. Six wells were trypsinized and the cells mixed 1:1 with Trypan blue stain (0.5% in PBS), and counted in a hemocytometer. The mean count was recorded. Adherent cells were left untreated (controls) or incubated with sFn, fibrinogen (0.5 mg/ml), GPRP-NH2 (4 mM) or thrombin (0.125 U/ml). After washing with RPMI, 5 µl of Calcein AM (Molecular Probes, Eugene, Oreg.) stock solution in DMSO were added to 5 ml of effector cell preparation (Leukocytes; 2×106 cells/ml) and incubated for 30 min at 370 C.

Effector cells were left untreated (controls) or incubated with sFn or fibrinogen (0.5 mg/ml), GPRP-NH2 (4 mM) or thrombin (0.125 U/ml). Total fluorescence was determined by addition of 200 µl of fluorescently labeled effector cells to three wells and fluorescence measured. Minimal fluorescence (blank) was measured in three wells containing adherent cells to which only RPMI is added. After a further wash, cells were made to 1×106/ml and 200 µl added to appropriate wells, and incubated at 37° C. for 1 h. The plates were washed three times with RPMI followed by addition of 200 µl of 0.5 M NaOH to lyse the cells. The supernatants were removed into black 96-well microtiter plates and fluorescence was measured on a Perkin-Elmer Victor 3 plate reader. Specific adherence was determined by: (Test-Blank/Total-blank)*100%.

Antibody Blocking of Cellular Adherence:

Lyophilized murine anti-human monoclonal blocking antibodies directed against $\alpha_L\beta2$ (clone 25.3) and CD54 (clone 84H10) were obtained from Beckman-Coulter (Miami, Fla.), as were purified immunoglobulin matched isotypic controls (IgG1 (mouse) Clone 679.1Mc7). Blocking monoclonal anti-£\M£]2 (clone ICRF44) was obtained from PharMingen (BD Biosciences, San Jose, Calif.). All antibody inhibition experiments were performed using pre-incubation of target cells with 5 µg antibody/106 cells.

Experiments were performed in triplicate wells and the results were expressed as the mean+SD for three separate experiments).

Measurement of Cellular Cytotoxicity:

Tumor cells were detached from plastic using trypsin (0.25%)/EDTA (0.1 µM), washed and resuspended in 2 ml of culture medium and counted. Cell aliquots were untreated or pretreated as described supra, depending on the experiment to be performed. The cell concentration was adjusted to 1×105 cells/ml and 100 µl added to the wells of a round-bottomed 96 well microtiter plate. One hundred microliters of untreated or appropriately preincubated monocytes were added to the tumor cells in appropriate wells at an effector target cell ratios of 20:1, and the plates were centrifuged at 250×g for 10 min and 100 µl of supernatant carefully removed into the appropriate wells of an optically clear 96 well flat bottomed plate. LDH activity was measured using a standard kit. (Roche Molecular Biochemicals, Indianapolis, Ind.).

One hundred microliters of reaction mixture were added to the wells and incubated at room temperature for 30 min in the dark. The absorbance of each well was measured using a Perkin-Elmer Victor 3 plate reader equipped to measure absorbance. Specific cytotoxicity was determined by (test release−blank/total release−blank)*100%. Initial experiments were performed to determine the optimum time course and effector:target (E:T) cell ratio for monocyte cytotoxicity. Based on these results, sFn inhibition studies were performed using an E:T ratio of 20:1 in an 18 h assay, which was consistent with other reports (Webb et al., 1991; McLachlan et al., 1995).

Monocyte Adherence to Tumor Cells Under Flow Conditions:

To simulate the fluid shear stresses present in vivo, coverslips containing Calcein AM labeled, adherent A375 were loaded into the FCS2 stage incubator (Bioptechs Inc., Butler, Pa.) and mounted on the stage of a Leica DMIRB inverted fluorescence microscope equipped with a Hamamatsu Color Chilled 3CCD camera (C5810 model) attached to a computer for data acquisition.

The FCS2 incubator is a closed near-laminar flow, temperature-controlled perfusion chamber which facilitates direct observation and scanning of the cells on the coverslip during perfusion with solutions or cell suspensions. It was designed to maintain accurate thermal control and allow high-volume near-laminar flow perfusion. A fluid pathway was formed (Dimensions 0.5 mm×14 mm×25 mm) by separating the microaqueduct slide from the coverslip containing cells with a single silicone gasket with a rectangular bore, generating nearlaminar flow conditions during perfusion. The stage incubator was initially connected to a peristaltic pump on the afferent side using 0.062 inch bore S/P medical grade silicone tubing (Fisher Scientific, Suwanee, Ga.), with a three way in-line tap closed to the incubator inlet. The efferent side was connected to waste. After connection of the electronic temperature control, the coverslips were perfused with RPMI to briefly buffer the cells at 37° C. for fifteen minutes (flow rate of 0.5 ml/min). The inlet was then connected to the tube containing the appropriately treated monocyte suspension (3 mL). The efferent tubing was also connected to the same tube, and Di-I (Gant et al., 1992) labelled monocytes were recirculated across the tumor cells for 1 h, after which, the tubing was set up to the initial configuration and the cells were again washed with RPMI for 10 min to remove unbound monocytes.

Individual still images in five randomly chosen fields of view were captured and stored on the computer. The number of monocytes (red) and tumor cells (green) were counted in each field of view and the mean monocyte/tumor cell ratio was calculated. The wall shear stress was calculated using the momentum balance for a Newtonian fluid. The viscosity of water at 37° C. was used as an approximation of the viscosity of the buffer used (RPMI 1640; 0.007 poise). As described in the following equation, the wall shear stress experienced by the monolayer is equal to: $T=3 \mu Q/2a^2 b$, where T=wall shear stress, µ=coefficient of viscosity (0.007 Poise), Q=volumetric flow rate (0.0083 cm3/s), a=half channel height (0.025 cm), and b=channel width (1.5 cm). The wall shear rate is given by T/µ. Experiments were conducted to maximize adherence in the model, within physiologically relevant shear rates (In post-capillary venules, shear rate has been reported to range between 35 and 560 s-1 (Lawrence et al., 1990; Heisig, 1968). This range is believed to be characteristic of the stresses that a leukocyte must resist to form a stable adhesion with a vessel wall).

Preparation of sFn Blocking Peptides:

Based on the reported activities of the various fibrin(ogen) blocking peptides, four were selected which would possibly also inhibit fibrin mediated immunosuppression (Table 1).

Stock Peptides:

Lyophilized peptides (50% purity) were obtained from Sigma-Genoysys (The Woodlands, Tex.). Peptides 1, 2, and 4 were each made up to a 100 µM stock concentration in PBS. Peptide 3 was first solubilized in a small amount of DMSO (on account of its hydrophobicity), followed by subsequent suspension in PBS, and was also made up to a 100 µM stock concentration. All peptides were divided into 50 µL aliquots, and stored at −20° C. Peptides were used at a working concentration of 4 µM.

Effect of sFn Blocking Peptides on Clot Formation in Purified Fibrinogen and in Recalcified Citrated Plasma:

Experiments were performed to determine if the specific fibrin(ogen) adherence inhibitors also affected (1) fibrinogen clotting in the presence of thrombin, or (2) normal coagulation in recalcified plasma.

Fibrinogen (0.5 mg/ml, 0.05 mmol/L), and thrombin (0.125 U/ml) were used at the concentration demonstrated to induce maximal inhibition of adherence and cytotoxicity in microplate assays. Thrombin (0.625 µl (stock 100 U/ml) was added to RPMI 1640 medium containing 25 µl (stock 10 mg/ml) thrombin alone or in the presence of 4 mmol/L specific peptide or peptide combination in a total volume of 1 ml. The tubes were left at room temperature and clotting was determined by observed gelation of the solution every 30 s, and the approximate clotting time was recorded. An additional control was also tested in which the fibrin polymerization inhibitor GPRP-NH2 was added to fibrinogen in the presence of P1-P4 prior to thrombin addition. The tube was left at room temperature to determine if clotting was observed.

The effect of the specific peptides on the clotting of re-calcified normal human plasma was also examined to determine if the normal coagulation cascade was inhibited in their presence. Plasma alone or in the presence of single or combined peptides P1-P4 (4 mM final concentration: 20 µl of 100 mM stock) was re-calcified with CaCl2 (50 µL; 25 mM stock) in a final volume of 500 µL. Tubes were left at room temperature and clotting time was then recorded.

Peptide Blocking of Cellular Adherence:

After fluorescence labeling of each cell type, stock peptides were added to both confluent coverslips and/or 1 milliliter suspensions of monocytes (P1 and P2) and/or sFn solution (P3 and P4) for a final treatment concentration of 4 mM (40 uL added to 1 mL suspension). Cells were treated with peptides for 20 minutes at room temperature, followed directly by washing of cells (by centrifugation and resuspension—monocytes, or perfusion with RPMI 1640 for 10 min—tumor cells). For sFn peptide treatment, peptides remained in the sFn solution during incubation. Monocyte adherence to tumor cells under flow conditions was then performed as described above.

Peptide Blocking of Fluorescently Labeled sFn Adherence to A375 Cells and Monocytes:

Oregon Green labeled fibrinogen was obtained from Molecular Probes (Oregon Green 488 human fibrinogen conjugate (F-7496)). Lyophilized stock fibrinogen (5 mg) was made up in RPMI 1640 to a total volume of 5 ml, aliquotted (25 µl) and stored at −200 C until time of experiment. For experiments, labeled sFn was prepared as described for sFn above, and incubated for 20 minutes at 370 C to allow sFn formation. Stock peptides (P1 and P2) were added to both confluent coverslips containing unlabeled A375 cells and/or 1 milliliter suspensions of unlabeled monocytes and/or labeled sFn (P3 and P4) at a final concentration of 4 mM, for 20 minutes at room temperature, followed by washing in RPMI 1640. Peptides were retained in the sFn solution during adherence. Untreated or peptide pretreated monocytes and/or tumor cells were incubated for 20 min with labeled-sFn (+/− peptide treatment as appropriate), and washed in RPMI 1640. The monocyte pellet was resuspended in 1 ml of phenol red free RPMI 1640 and 10 µl added to a microscope slide, coverslipped and sealed for microscopy.

Coverslips containing tumor cells were inverted onto a microscope slide together with 50 µl of Pro-long Gold™ (Molecular Probes) mounting medium, and allowed to harden for microscopy. An Olympus BX61 was used (100× oil immersion objective) to observe samples and capture images. Using the same microscope settings to observe differences in fluorescence between samples, five representative fields were captured of each slide for each pretreatment. Images were processed using Image Pro Plus™ (Media Cybernetics, Silver Spring, Md.) and deconvolved using AutoDeblur™ deconvolution software (Media Cybernetics, Silver Spring, Md.).

Statistical Analysis:

In static microplate adherence and cytotoxicity assays (FIGS. 4, 5 and 12), each data point was obtained as the mean+/− SD for three replicates. Each experiment was performed at least three times. Student's t-test for independent (unpaired) variables was used to determine significant differences between groups.

For experiments investigating adherence under flow conditions (FIGS. 13 and 14), each experiment used monocytes from a single individual and the experiment was internally controlled on each occasion by inclusion of untreated and sFn/sFn treated cells. Each experiment was performed at least five times. Inhibition of adherence compared to the untreated control, as well as peptide blocking of sFn inhibition was determined by direct comparison with its own internal control in each experimental protocol. Thus, the number of untreated and sFn treated controls was greater than the number of tests for each single or combined peptide. Since there was also variation in monocyte adherence from individual donors, each peptide effect was compared to the whole population of either untreated or sFn treated control, using Student's t-test for independent (unpaired) variables.

Figure 4:
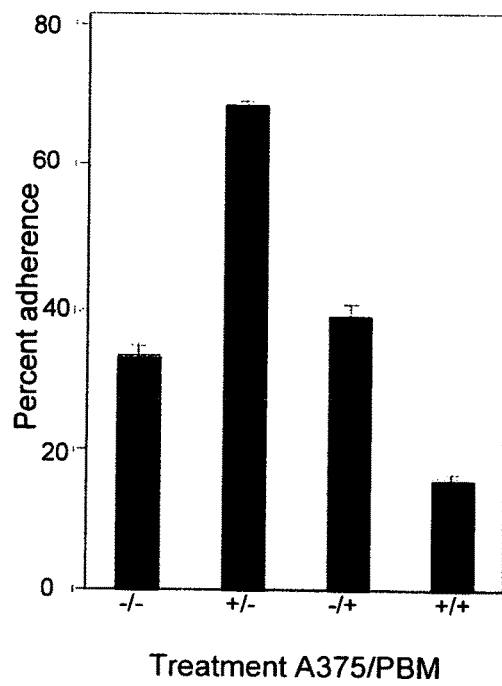
FIG. 4 shows the effect of soluble fibrin on monocyte adherence to tumor cells. Calcein AM labeled PBM incubated with A375 cells after pre-treatment of A375 and/or PBM with RPMI or sFn prior to assay. sFn pre-treatment of tumor cells significantly increased adherence to untreated A375 cells compared to the untreated control (P<0.01: n=3). Preincubation of monocytes also marginally increased adherence to untreated A375 cells (P<0.05: n=3) compared to the untreated control, but to a significantly lower degree than with sFn treated A375 cells (P<0.01 compared to monocyte sFn). sFn pre-treatment of both effector and target cells resulted in a significant inhibition of adherence (P<0.05: n=3) compared to the untreated control.

Effect of sFn on Monocyte/Tumor Cell Adherence in Static Microplate Assays:

Experiments were performed to determine the effect of sFn pre-incubation of either monocytes, tumor cells, or both on monocyte adherence to A375 melanoma cells in static microtiter plate assays (FIG. 4). In the absence of sFn, monocytes adherence was 32.9+1.3%. Pretreatment of tumor cells with sFn significantly (P<0.01 compared to untreated control) increased adherence (68.5+0.7%). Addition of sFn treated monocytes to untreated tumor cells also increased adherence (38.75+1%; P<0.05 compared to untreated control), but to a significantly lower degree than tumor cell pretreatment with sFn (P<0.01 compared to sFn treated tumor cells). However, when monocytes and tumor cells were both pre-treated with sFn a pronounced inhibition of adherence was observed (15.95+1%; P<0.01 compared to untreated control).

Effect of sFn on Monocyte Cytotoxicity Against Tumor Cells in Static Microplate Assays:

Monocyte cytotoxicity against A375 melanoma cells was measured in a static microplate assay (FIG. 5). At an effector:target cell ratio of 20:1 monocyte cytotoxicity was 28.6+0.7%. Pretreatment of A375 cells with sFn did not significantly (P>0.05) affect cytotoxicity (27.1+0.7%) compared to the untreated control, but a significant reduction (P<0.05) was observed when monocytes were sFn treated (20+0.7%). Maximal inhibition of cytotoxicity compared to untreated cells was observed when both effector and target cells were sFn treated (17.3+0.3%; P<0.01 compared to Untreated control, sFn treated monocytes and to sFn treated A375 cells; n=3).

Effect of Shear Rate on Monocyte Adherence to Tumor Cells Under Flow Conditions:

Initial experiments were conducted to maximize adherence in the model, within physiologically relevant shear rates. FIG. 10 shows the percentage adherence (number of monocytes/field/number of tumor cells/field) at flow rates of 0.5-2.5 ml/min. Maximal monocyte adherence was observed at a flow rate of 0.5 ml/min corresponding to a shear stress of 0.93 dynes/cm2, with a corresponding shear rate of 132.9 s-1. This shear rate was within the range of the stresses (35 and 560 s-1) (Lawrence et al., 1990; Heisig, 1968) which a leukocyte must resist to form a stable adhesion with a postcapillary vessel wall. Experiments investigating sFn inhibition of adherence were performed in further experiments at a flow rate of 0.5 ml/min. FIGS. 11A-11B show two representative images of monocytes (red) adherent to tumor cells (green). In FIG. 11A untreated monocytes were adhered to untreated tumor cells. Less adherence was observed when both cells were pre-treated with sFn (FIG. 11B).

Effect of sFn and Monoclonal Anti-$\alpha_L\beta2$, $\alpha_M\beta2$ and CD54 on Monocyte/Tumor Cell Adherence Under Flow Conditions:

Pre-treatment of monocytes with monoclonal anti-$\alpha_L\beta2$ antibody (5 µg/$10^6$ cells) inhibited their adherence to untreated A375 cells by 80+7%. (FIG. 12), whereas only 23+0.3% inhibition was observed when A375 cells were also pre-treated with sFn (P<0.05 compared to untreated A375 cells). Conversely, monocyte pre-treatment with anti-$\alpha_M\beta2$ monoclonal antibody only inhibited adherence by 22.5+ 2.6% to untreated A375 cells, and by 80+0.5% to sFn pretreated tumor cells (P<0.05 compared to untreated A375 cells). Incubation of A375 cells with anti-CD54 inhibited monocyte adherence of untreated monocytes by 53+0.3%, and sFn pretreated monocytes by 86+0.2%, which were significantly greater (P<0.05) compared to untreated monocytes). Pre-incubation of either cell type with appropriate isotypic control or an irrelevant antibody (CD4) did not significantly (P>0.05) inhibit adherence.

Effect of $\alpha_M\beta2$ and CD54 Specific Blocking Peptides on Thrombin Induced Fibrin Polymerization:

Experiments were performed to determine if fibrin(ogen) blocking peptides affected the ability of fibrinogen to clot. Using purified fibrinogen in the absence or presence of P1+P2, P3+P4, or all four peptides together, clotting was observed within approximately 5 minutes. Addition of GPRP-NH2 to purified fibrinogen prior to thrombin addition failed to clot within 15 minutes, indicating the production of soluble, rather than polymerized fibrin. Using no treatment, or the same combinations of peptides, clotting of recalcified plasma was observed under all conditions in approximately 4 minutes.

Effect of sFn, $\alpha_M\beta2$ and CD54 Specific Blocking Peptides on sFn Inhibition of Monocyte/Tumor Cell Adherence Under Flow Conditions:

FIG. 13 shows the effect of two specific peptides, designated P1 and P2 on sFn inhibition of monocyte adherence to A375 melanoma cells in a flowing microscope stage incubator. P1 represents the sFn major binding site for CD54 and P2 represents the sFn major binding site for $\alpha_M\beta2$. From the left, the first bar (+/+) shows the mean (+SD) inhibition when both monocytes and tumor cells were pre-incubated for 20 min with sFn. SFn considerably reduced monocyte adherence (P<0.05 compared to untreated cells).

When both monocytes (which express $\alpha_M\beta2$ and some CD54) and tumor cells were pre-treated with both P1 and P2 followed by sFn prior to assay (Bar2+P1P2/+P1/P2), sFn inhibition was considerably reduced to a level that was not significantly different from the untreated control. This level of sFn inhibition was also observed when cells were treated with peptides in the absence of sFn (Bar3; P1P2/P1/P2). These results suggest that blocking the major receptor sites for sFn on $\beta_M\beta2$ and CD54 blocked binding of sFn, thus allowing $\beta_L\beta2$ (LFA1 which does not bind to sFn) and $\alpha_M\beta2$ to bind to CD54, thereby restoring adherence. If A375 cells are treated with P1 to block CD54 binding to fibrin (even when sFn was added subsequently) and monocytes are treated with sFn, inhibition was still observed (Bar4; +P1/+) since CD54 was blocked by P1. Similarly, inhibition was still observed when monocytes were treated with P2 to block sFn binding to $=_M\beta2$, and tumor cells were treated with sFn (Bar 5; +/+P2). As controls, tumor cells were incubated with P1 (but not sFn) and monocytes were treated with sFn. Inhibition was still observed because P1 blocked sFn coated $\alpha_M\beta2$ binding (Bar 6; P1/+).

Inhibition was also observed when P2 blocked sFn binding to monocytes and tumor cells were treated with sFn (Bar 7; +/P2). The final 3 bars (Fg/Fg, thr/thr, GPRPNH2/GPRP-NH2) showed that no significant (P>0.05 compared to untreated cell adherence) inhibition was observed when cells were treated with soluble fibrinogen, thrombin, or GPRPNH2). These results demonstrate the peptides P1 and P2 are effective in inhibiting sFn inhibition of monocyte adherence by a mechanism involving its blocking of CD54 to $\alpha_M\beta2$. FIG. 14 shows the effect of two specific peptides, designated P3 and P4 on sFn inhibition of monocyte adherence to A375 melanoma cells in a flowing microscope stage incubator. P3 represents the CD54 major binding site for sFn and P4 represents the $\alpha_M\beta2$ major binding site for sFn. From the left, the first bar (+/+) shows the mean (+SD) when both monocytes and tumor cells were pre-incubated for 20 min with sFn. SFn considerably reduced monocyte adherence (P<0.05 compared to untreated cells). Pre-treatment with sFn with P3 and P4 prior to its incubation with tumor cells and monocytes (which should block its binding) resulted in a marked increase in cell adherence, which was not significantly different than the untreated control (Bar 2; +P3P4/+P3P4; P<0.05), thus reversing sFn inhibition of adherence. As expected, addition of peptides P3 and P4 to cells did not significantly affect adherence (Bar 3; –P3P4/–P3P4; P>0.05 compared to untreated).

When sFn was treated with P3 and incubated with tumor cells, and monocytes were untreated, little or no inhibition was observed, because $\alpha_M\beta2$ could still bind to CD54 directly (Bar4; +P3/–). Similarly, when sFn was pre-treated with P4 and incubated with monocytes, and tumor cells were untreated, no inhibition was observed, because tumor cells would not bind P3-sFn, and the sFn on the monocytes could bind to CD54 on the tumor cells (Bar 6; +P3/+). Similarly, when sFn was pre-treated with P4 and incubated with monocytes, and tumor cells were incubated with sFn, no inhibition was observed, because the free $\alpha_M\beta2$ could still bind to sFn on the tumor cells (Bar 7; +/+P4). These results show that blocking of sFn with peptides representing its major CD54 and $\alpha_M\beta2$ receptor sites effectively inhibited its ability to block adherence of monocytes to tumor cells.

Effect of $\alpha_M62$ and CD54 Specific Blocking Peptides on sFn Adherence to Monocytes and Tumor Cells:

Having demonstrated that specific sFn blocking peptides reversed sFn inhibition of monocyte/tumor cells adherence, experiments using fluorescently labeled fibrinogen to prepare sFn were performed to observe whether sFn binding to cells was also decreased. After sFn binding (+/−) peptide pre-treatment, slides were observed on an Olympus BX61 fluorescence microscope equipped with an Olympus (COOL-1300QS) digital camera for image acquisition. Oregon Green fluorescence was detected using a 535 nm long-pass dichroic filter. After setting up the microscope to detect tumor cells or monocytes, all settings were kept identical for subsequent slides. FIG. 15 shows binding of FITC-sFn to A375 cells (FIG. 15A). Fluorescent sFn bound strongly to both the cell types. However, when tumor cells were pre-treated with P1+P3 (FIG. 15B), or sFn was pre-treated with P3+P4 (FIG. 15C), almost no binding was observed. Similarly, sFn bound strongly to monocytes (FIG. 15D). Monocyte Pre-incubation with P1+P2 considerably reduced sFn fluorescence, as did sFn pre-incubation with P3+P4, demonstrating that the blocking peptides cause reduced sFn binding to cells.

Example 4

Measurement of sFn Monomar in Prognostic Study

Plasma samples: Approximately 1000 plasma samples were collected and stored from patients with bladder cancer (N=300), breast cancer (N=300) and controls with benign breast disease (N=70), and additional samples from other common cancers including lung cancer, melanoma, and colorectal cancer (N=300). These samples were stored at −70 C for a duration of time between 1 and 10 years. Fresh samples were also collected from a range of healthy individuals to serve as a control group (N=53). All samples were coded, as to perform a blind study to quantitate levels of soluble fibrin in plasma samples using the STA LIATEST FM kit (N=656).

STA® LIATEST FM (Diagnostica Stago, France; Catalog #00984):

The STA® LIATEST FM (Lot No. 060631) is an immuno-turbidimetric assay for the quantitative determination of fibrin monomer on the STA Compact machine. The principle of the test involves a reagent made of latex microparticles on which monoclonal antibodies specific for fibrin monomer (mouse monoclonal anti-human fibrin monomer antibodies) are coated. When the latex reagent is mixed with the sample plasma, an antigen-antibody reaction takes place, leading to the agglutination of the latex microparticles. The increase of absorbance which is recorded is proportional to the quantity of fibrin monomer present in the sample. The detection limit of the test is 5 μg/mL, and the working range is 5-150 μg/ML. No dose-hook effect has been observed with levels up to 400 μg/mL.

Normal levels of soluble fibrin monomer have been reported to be approximately 6.0 μg/mL in healthy individuals. Given this, it can be concluded that approximately half of the tested samples had levels higher than this.

TABLE 2

| Concentration of sFn in plasma samples (N = 656 plasma samples) | |
| --- | --- |
| Measured sFn Concentration Range: | 5-150 ng/mL |
| Normal Concentration (<6.0 μg/mL): | 341 samples |
| Abnormal Concentration (>6.0 μg/mL): | 315 samples |

The following References Were Cited Herein:
Abbassi, O. et al., 1993, *Blood Cells* 19, 245-259.
Adams, D. H. et al., 1997, *Br. J. Cancer* 75, 1421-1431.
Aebersold, P. et al., 1991, *J. Natl. Cancer Inst.* 83, 932-937.
Altieri, D. et al., 1995, *JBC Online.* 270(2). 696-699.
Andrassy, K. et al. 1980, *Klin. Wochenschr.* 58, 91-97.
Agger, R. & Hokland, M. E., 2000, *Ugeskr. Laeger* 162, 4377-4381.
Barkalow, F. J. et al., 2000, *Blood* 96, 3070-3077.
Becker, J. C. et al., 1992, *Immun. Infekt.* 20, 62-63 (1992).
Beekhuizen, H. & Van Furth, R, 1993, *J. Leukoc. Biol.* 54, 363-378.
Biggerstaff et al., 1999, *Clin Exp Metastasis.*, 17, 723-730.
Bynum, L J. et al., 1976, *Am Rev Respir Dis.* 114(2). 285-9.
Carreno, M. P. et al., 1995, *Allerg. Immunol.* (Paris) 27, 106-110.
Carlos, T. M. & Harlan, J. M., 1994, *Blood* 84, 2068-2101.
Clark, W. et al., 1988, *Immunol. Rev.* 103, 37-51.
D'Souza, S. et al., 1996, *JBC Online.* 271(39). 24270-24277.
Duncan, A. et al., 1997, *Thromb. Haemost.* (Suppl. Abstract) 123
Esumi, N. et al., 1991, *Cancer Res.* 51, 4549-4556.
Forsyth, C. B. et al., 2001, *J. Exp. Med.* 193, 1123-1133.
Fortis, C. et al., 1995, *Clin. Immunol. Immunopathol.* 76, 142-147.
Fu, H. et al., 2001, *Hua Xi. Yi. Ke. Da. Xue. Xue. Bao.* 32, 21-23.
Fukui, Y. et al., 1988, *J. Invest Dermatol.* 91, 319-322.
Gant et al., 1992, *J Immunol Methods.* 156(2), 179-189.
Gardiner and D'Souza, 1997, *J Biol Chem,* 271(24), 15474-15480.
Heisig, 1968, *Adv Microcirc* 1, 89-94.
Lawrence et al., 1990, *Blood,* 75(1), 227-237.
McLachlan et al., 1995, J Immunol. 154(2), 832-843.
Ugarova et al., 1998, *J Biol Chem.* 273, 22519-22527.
Webb et al., 1991, *J Immunol.* 146(10), 3682-3686.
Yakovlev et al., 2005, Biochemistry 18; 44(2), 617-626.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

What is claimed is:

1. A method of treating an individual diagnosed with a cancer, comprising:
   administering to the individual an anticancer agent; and
   administering to the individual pharmacologically effective amounts of a pharmaceutical composition comprising a mixture of isolated peptides selected from one of
   i) a combination of SEQ ID NO: 5 or a recombinant peptide thereof and SEQ ID NO: 6 or a recombinant peptide thereof, or
   ii) a combination of SEQ ID NO: 3 or a recombinant peptide thereof and SEQ ID NO: 7 or a recombinant peptide thereof,
   said pharmaceutical composition effective to reduce inhibition of cell adherence due to the soluble fibrin, restore immune response, inhibit progression of a solid tumor, inhibit enhancement of metastasis of the cancer or a combination thereof in the individual, thereby treating the individual diagnosed with the cancer.

2. The method of claim 1, wherein the anticancer agent is administered concurrently with the administration of the pharmaceutical composition, wherein the dosage of the anticancer agent is lower than the dosage normally required to have at least a minimally pharmacological or therapeutic effect against the cancer.

3. The method of claim 2, wherein the cancer is melanoma, leukemia, renal cell carcinoma, small cell lung cancer, prostate cancer, breast cancer or any cancer wherein the cancer cell binds to soluble fibrin.

4. The method of claim 2, wherein the cancer is a metastatic cancer.

5. The method of claim 4, wherein the metastatic cancer is a blood-borne or lymphatic metastatic cancer, wherein said cancer is melanoma renal cell carcinoma, small cell lung cancer, prostate cancer, breast cancer or any cancer wherein the cancer cell binds to soluble fibrin.

6. The method of claim 2, wherein the peptides is a mixture of SEQ ID NO: 3 or a recombinant peptide thereof and SEQ ID NO: 7 or a recombinant peptide thereof.

7. The method of claim 2, wherein the cell is an immune cell, an endothelial cell or a tumor cell.

* * * * *